(12) United States Patent
Lao et al.

(10) Patent No.: US 8,349,563 B2
(45) Date of Patent: Jan. 8, 2013

(54) SEQUENCE AMPLIFICATION WITH TARGET PRIMERS

(75) Inventors: Kai Lao, Pleasanton, CA (US); Neil Straus, Emeryville, CA (US); Nanlan Xu, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 216 days.

(21) Appl. No.: 12/581,095

(22) Filed: Oct. 16, 2009

(65) Prior Publication Data

US 2010/0124765 A1    May 20, 2010

Related U.S. Application Data

(60) Provisional application No. 61/115,833, filed on Nov. 18, 2008.

(51) Int. Cl.
*C12Q 1/68* (2006.01)
*C12P 19/34* (2006.01)

(52) U.S. Cl. ...................................... 435/6.12; 435/91.2

(58) Field of Classification Search .................. None
See application file for complete search history.

(56) References Cited

U.S. PATENT DOCUMENTS

| | | |
|---|---|---|
| 2004/0014129 A1 | 1/2004 | Brown |
| 2006/0105348 A1 | 5/2006 | Lee et al. |
| 2007/0048757 A1 | 3/2007 | Lao et al. |
| 2007/0077570 A1 | 4/2007 | Lao et al. |
| 2008/0161197 A1 | 7/2008 | Lao |
| 2009/0023190 A1 | 1/2009 | Lao et al. |

FOREIGN PATENT DOCUMENTS

| WO | WO-0059323 | 10/2000 |
|---|---|---|
| WO | WO-2010/059323 | 8/2010 |

*Primary Examiner* — Kenneth R. Horlick
*Assistant Examiner* — David Thomas

(57) ABSTRACT

The present disclosure relates to the amplification of target nucleic acid sequences for various sequencing and/or identification techniques. This can be accomplished via the use of target primers. The use of these target primers, as described herein, allows for the reduction in the amplification of undesired hybridization events (such as primer dimerization) while allowing for the amplification of the target nucleic acid sequences.

35 Claims, 18 Drawing Sheets

SEQUENCE AMPLIFICATION WITH TARGET PRIMERS

SEQUENCE LISTING

The instant application contains a Sequence Listing which has been submitted via EFS-Web and is hereby incorporated by reference in its entirety. Said ASCII copy, created on Jan. 8, 2010, is named 6972 US.txt, and is 3,126 bytes in size.

FIELD

The invention relates to methods and compositions for amplifying nucleic acid sequences.

INTRODUCTION

Whole transcriptome amplification (WTA) can be a valuable technique for amplification of a transcriptome from minimal or limiting amounts of nucleic acids for subsequent molecular genetic analysis.

Following a reverse transcription step, whole transcriptome amplification can involve either conventional or nonconventional PCR amplification methods. Conventional PCR entails the amplification and subsequent detection of specific DNA sequences that are precisely characterized in length and sequence using nondegenerate primers, while random, "nonconventional" PCR involves universal amplification of prevailing DNA or amplification of unknown intervening sequences which are not generally defined in length or sequence using degenerate primers.

SUMMARY

In some embodiments, a method is provided for nucleic acid amplification. The method can comprise, consist, or consist essentially of providing a first primer that comprises a 3' target specific region and a universal region and contacting the first primer and a target nucleic acid sequence such that the 3' target specific region hybridizes to the target nucleic acid sequence. The first primer is extended to produce an extended primer. A second primer (that also includes the universal region) is then hybridized to the extended primer. The second primer is then extended to form a double extended primer. The 3' target specific region of the first primer can include a sequence that will bias its hybridization to RNA, such as, for example, mRNA.

In some embodiments, the invention comprises a kit. The kit can comprise a first primer comprising a first 3' target specific region, wherein the 3' target specific region comprises at least 6 thymines and a universal region. The kit can further comprise a second primer comprising a second 3' target specific region and the universal region.

In some embodiments, the invention comprises a method for nucleic acid amplification. The method can comprise producing an extended primer by performing a reverse transcription reaction on a target nucleic acid sequence using a first primer comprising a first 3' target specific region and a 5' universal region. The first 3' target specific region comprises at least 6 thymines. The method can further comprise hybridizing a second primer to the extended primer. The second primer comprises a second 3' target specific region and the 5' universal region. The method can further comprise extending a nucleic acid sequence from the second primer using the extended primer as the template for the extension, thereby forming a double extended primer. The method can further comprise allowing the double extended primer to self-hybridize. The self hybridization occurs via the universal region and a sequence that is complementary to the universal region, thereby forming a looped section between the universal region and the sequence that is complementary to the universal region. The method can further comprise adding a third primer that is complementary to an insert section within the double extended target primer and performing a PCR amplification to amplify the insert section.

In some embodiments, the invention comprises a method for nucleic acid amplification. The method can comprise performing a reverse transcription reaction on a target nucleic acid sequence to produce a cDNA of the target nucleic acid sequence. The method can further comprise introducing a universal region into the cDNA of the target nucleic acid sequence or the complement of the cDNA of the target nucleic acid sequence. The method can further comprise introducing a complement to the universal region into the cDNA of the target nucleic acid sequence or the complement of the cDNA of the target nucleic acid sequence, thereby forming a double extended target primer. The method can further comprise allowing the double extended target primer to self-hybridize. The self hybridization occurs via the universal region and the complement to the universal region and thereby forms a looped section between the universal region and the sequence that is complementary to the universal region. The method can further comprise adding an insert primer that is complementary to an insert section within the double extended target primer. The method can further comprise performing a PCR amplification to amplify the insert section.

BRIEF DESCRIPTION OF THE DRAWINGS

FIG. 8 discloses SEQ ID NOS 6 and 7, respectively, in order of appearance.

FIG. 9 discloses SEQ ID NOS 6 and 7, respectively, in order of appearance.

FIG. 10A discloses SEQ ID NOS 8, 9 and 1, respectively, in order of appearance.

DETAILED DESCRIPTION OF VARIOUS EMBODIMENTS

Figure 1A:
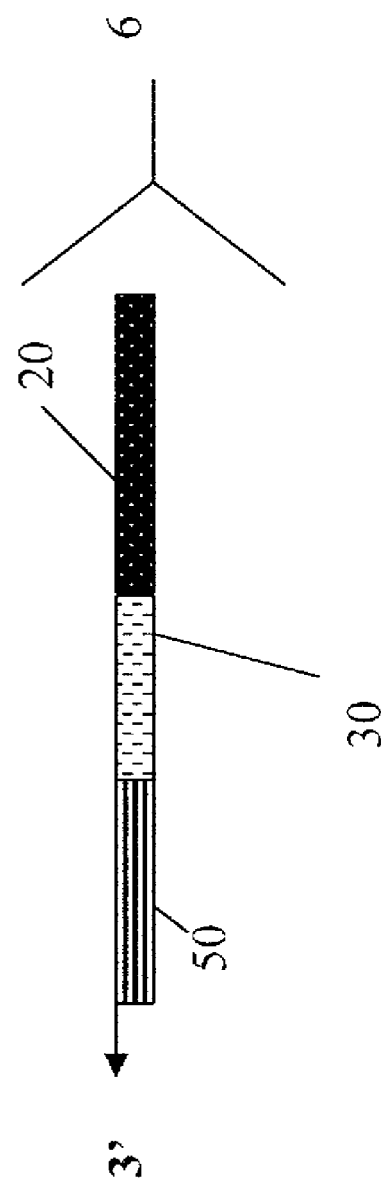
FIG. 1A depicts one embodiment of a linear target primer.

The use of various primers in the amplification of a target nucleic acid sequence is described herein. In some embodiments, this involves the use of primers to put complementary sequences on both ends of a target nucleic acid sequence. Products that include insert sections that are very short (including no insert sections, such as primer dimers) will effectively self-terminate from subsequent amplification, as they will rapidly self-hybridize. Products that include an insert section that is relatively long can remain viable templates for continued amplification. Thus, primer dimers and other short products are selectively removed from the amplification process.

As will be appreciated by one of skill in the art, in light of the present disclosure, general amplification of mRNA faces various obstacles. For example, most of a cells' RNA is ribosomal RNA and tRNA. Thus, whole transcriptome amplification is dominated by ribosomal sequences, which can make the resulting amplified cDNA useless for Sanger sequencing or even massive parallel sequencing. Alternative approaches, such as fractionating the RNA into poly-A+RNA and amplifying mRNA can be impractical when small sample size, such as RNA from a single cell, is being used. While it is possible to use the poly-A tail of the mRNA as a primer target, one issue that results from this is that the resulting libraries will be 3' biased. As disclosed herein, this can be acceptable, if one can make these libraries as meaningful as possible.

In some embodiments, effective amplification of target sequences can be achieved by using at least two different target primers in an amplification method. In some embodiments, the first target primer can include a poly-thymine sequence at its 3' end and be employed for reverse transcription of the mRNA, thereby producing an extended target primer. The first target primer will also include a universal region at its 5' end. In some embodiments, the second target primer can comprise a random and/or degenerate 3' end, and thereby hybridize to the extended target primer. The second target primer will also include the same universal region as the first target primer. In some embodiments, the second target primer can comprise a 3' target specific region that is a specific sequence, such as a sequence that will hybridize to a splice site (e.g., 5' (A/C)AGG3'), and thereby hybridize to the extended target primer and further allow selective amplification of the mRNA. This embodiment can have additional advantages as it can be very selective in amplifying mRNA sequences as both the first and the second primer are relatively mRNA specific. In some embodiments, the use of the first and second target primers allows for a RNA population to be amplified while still reducing adverse effects of primer dimers The above and additional embodiments are described in greater detail below. Following the definition and alternative embodiments section provided immediately below, a general description of how target primers generally work is provided. Following this section, various specific embodiments relating to RNA amplification via target primers are described. Following this section, a brief description providing additional embodiments is provided along with a series of specific examples.

Some Definitions and Alternative Embodiments

As used herein, the term "target nucleic acid sequence" refers to a polynucleotide sequence that is sought to be detected, sequenced, and/or characterized in a sample. The target nucleic acid sequence can be obtained from any source and can include any number of different compositional components. For example, the target can be nucleic acid (e.g. DNA or RNA), transfer RNA, mRNA, siRNA, and can include nucleic acid analogs or other nucleic acid mimic. The target can be methylated, non-methylated, or both. The target can be bisulfite-treated and non-methylated cytosines converted to uracil. Further, it will be appreciated that "target nucleic acid sequence" can refer to the target nucleic acid sequence itself, as well as surrogates thereof, for example amplification products, and native sequences. In some embodiments, the target nucleic acid sequence is a miRNA molecule. In some embodiments, the target nucleic acid sequence lacks a poly-A tail. In some embodiments, the target nucleic acid sequence is a short DNA molecule derived from a degraded source, such as can be found in, for example but not limited to, forensics samples (see for example Butler, 2001, Forensic DNA Typing: Biology and Technology Behind STR Markers). In some embodiments, the target nucleic acid sequences of the present teachings can be present or derived from any of a number of sources, including without limitation, viruses, prokaryotes, eukaryotes, for example but not limited to plants, fungi, and animals. These sources can include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil samples), research samples generally, purified samples generally, cultured cells, and lysed cells. In some embodiments, while the target to be assayed is mRNA, the nucleic acid sequence involved in the method is derived from the mRNA, and thus need not be mRNA itself. Thus, in some embodiments, no (or no substantial amount of) target mRNA is actually present in the reaction mixtures or samples to which the first and/or second target primers are to be added.

It will be appreciated that target nucleic acid sequences can be isolated or obtained from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809, mirVana RNA isolation kit (Ambion), etc. It will be appreciated that target nucleic acid sequences can be cut or sheared prior to analysis, including the use of such procedures as mechanical force, sonication, heat, restriction endonuclease cleavage, or any method known in the art. Cleaving can be done specifically or non-specifically. In general, the target nucleic acid sequences of the present teachings will be single stranded, though in some embodiments the target nucleic acid sequence can be double stranded, and a single strand can be produced by denaturation.

As will be appreciated by one of skill in the art, the term "target nucleic acid sequence" can have different meanings at different points throughout the method. For example, in an initial sample, there can be a target nucleic acid sequence that is 2 kb in length. When this is amplified by the target primer to form a double-extended target primer, part of the target nucleic acid sequence can be contained within the double-extended target primer; however, not all of the target nucleic acid sequence need be contained within the double-extended target primer. Regardless of this, the section of the target nucleic acid sequence that is amplified can still be referred to as the "target nucleic acid sequence" (in part because it will still indicate the presence or absence of the large target nucleic acid sequence of which it is a part). Similarly, when the section of the insert section, which contains the target nucleic acid sequence, is amplified by the insert amplification primers it can also be described as amplifying the "target nucleic acid sequence." One of skill in the art will appreciate that, likely, the length of the target nucleic acid sequence will decrease as the sequence is processed further. When desired, each target nucleic acid sequence in each step can be specifically designated as an "initial target nucleic acid sequence," a "double-extended target primer target nucleic acid sequence", and an "insert section target nucleic acid sequence." Additionally, one of skill in the art will appreciate that the sequence that one is interested in determining if present in a sample can be a separate sequence from a target nucleic acid sequence that is amplified. For example, the sequences can be in linkage disequilibrium or from a different part of a gene or stretch of nucleic acids. Such sequences can be termed "inquiry target nucleic acid sequences."

The term "whole transcriptome amplification" does not require that 100% of a transcriptome be amplified. Rather, partial amounts of the transcriptome can be amplified and still qualify as a whole transcriptome amplification process. The above term simply denotes that amplification across a transcriptome has occurred, and can be interpreted to mean transcriptome wide amplification. The amplification process is one that amplifies a significant portion of the transcriptome nucleic acid in a sample. In some embodiments, the significant portion is at least 30%, for example, 30, 30-40, 40-50, 50-60, 60-70, 70-80, 80-90, 90-95, 95-98, 98-99, 99-100% of the transcriptome nucleic acid in a sample. As will be appreciated by one of skill in the art, the transcriptome nucleic acid need not be directly derived from a biological host and can itself be the result of some previous manipulation or amplification.

Unless explicitly denoted, the term "target primer" can refer to both or either a "linear primer" or a "loopable primer." Thus, "target primer" is a genus that includes both "linear primer" and "loopable primer".

As used herein, the term "loopable primer" refers to a molecule comprising a 3' target specific portion, a stem (comprising a first loop forming region and a second loop forming region), and an insert portion (which can optionally includes a noncomplementary region and will include a universal region). Illustrative loopable primers are depicted in FIG. 1C and elsewhere in the present teachings. It will be appreciated that the loopable primers can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N. A. R. 2001, vol 29:2437-2447, and Pellestor et al., Int J Mol. Med. 2004 April; 13(4):521-5), references cited therein, and recent articles citing these reviews. It will be appreciated that the selection of the loopable primers to query a given target nucleic acid sequence, and the selection of which collection of target nucleic acid sequence sequences to query in a given reaction with which collection of loopable primers, will involve procedures generally known in the art, and can involve the use of algorithms to select for those sequences with minimal secondary and tertiary structure, those targets with minimal sequence redundancy with other regions of the transcriptome, those target regions with desirable thermodynamic characteristics, and other parameters desirable for the context at hand. In some embodiments, the loop includes one or more additional nucleic acids that serve a desired function. In some embodiments, a universal region is included within the loop. In some embodiments, a noncomplementary region or sequence is included within the loop. In some embodiments, an identifying portion is included within the loop.

As will be appreciated by one of skill in the art, even though a primer is "loopable" it may not always be in its looped form. For example, at high temperatures or salt conditions, the two loop forming regions can separate from one another. However, even in situations where the loopable primer is not actually looped, it can still be referred to as a "loopable primer." Thus, the term "loopable primer" does not require that the primer actually be in the looped configuration.

As used herein, the term "linear primer" refers to a molecule comprising a 3' target specific portion and a universal region. It will be appreciated that the linear primers can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N. A. R. 2001, vol 29:2437-2447, and Pellestor et al., Int J Mol. Med. 2004 April; 13(4):521-5), references cited therein, and recent articles citing these reviews. It will be appreciated that the selection of the linear primers to query a given target nucleic acid sequence, and the selection of which collection of target nucleic acid sequence to query in a given reaction with which collection of linear primers, will involve procedures generally known in the art, and can involve the use of algorithms to select for those sequences with desirable features, such as, minimal secondary and tertiary structure, those targets with minimal sequence redundancy with other regions of the transcriptome, those target regions with desirable thermodynamic characteristics, and other parameters desirable for the context at hand. In some embodiments, a universal primer is included within the linear primer. In some embodiments, a noncomplementary region or sequence is included within the linear primer. In some embodiments, an identifying portion is included within the linear primer.

As used herein, the term "3' target-specific portion," "3' target specific region," or "3' target region" refers to a single stranded portion of a target primer that is complementary to at least a portion of a target nucleic acid sequence. The 3' target-specific portion is located downstream from the universal region and/or noncomplementary region of the target primer. Generally, the 3' target-specific portion is between 4 and 15 nucleotides long and can be between 6 and 12 nucleotides in length. In some embodiments, the 3' target-specific portion is 7 nucleotides long. It will be appreciated that, in light of the present disclosure, routine experimentation can be used to optimize length, and that 3' target-specific portions that are longer than 8 nucleotides or shorter than 6 nucleotides are also contemplated by the present teachings. In some embodiments, modified bases such as LNA can be used in the 3' target specific portion to increase the stability, for example by increasing the Tm of the target primer (see for example Petersen et al., Trends in Biochemistry (2003), 21:2:74-81). In some embodiments, universal bases can be used in the 3' target specific portion, for example to allow for smaller libraries of target primers. Universal bases can also be used in the 3' target specific portion to allow for the detection of unknown targets (e.g., targets for which specific binding sequences are not known). For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity.

In some embodiments, the 3' target-specific region includes or is a degenerate region, a random region, a specific region, or a known sequence. In some embodiments, the 3' target specific region includes a combination of these regions. In some embodiments, the 3' target specific regions have a Tm of between about 5° C. and 50° C. In some embodiments, a 15-mer has a Tm of less than about 60° C.

The term "degenerate primer" when used herein refers to a mixture of similar primers with differing bases at the varying positions (Mitsuhashi M, J Clin Lab Anal, 10(5):285 93 (1996); von Eggeling et al., Cell Mol Biol, 41(5):653 70 (1995); (Zhang et al., Proc. Natl. Acad. Sci. USA, 89:5847 5851 (1992); Telenius et al., Genomics, 13(3):718 25 (1992)). Such primers can include inosine as inosine is able to base pair with adenosine, cytosine, guanine or thymidine. Degenerate primers allow annealing to and amplification of a variety of target sequences that can be related. Degenerate primers that anneal to target DNA can function as a priming site for further amplification. A degenerate region is a region of a primer that varies, while the rest of the primer can remain the same. Degenerate primers (or regions) denote more than one primer and can be random. A random primer (or regions) denotes that the sequence is not selected, and it can be degenerate but does not have to be. In some embodiments, the 3' target specific regions have a Tm of between about 5° C. and 50° C. In some embodiments, a 15-mer has a Tm of less than about 60° C. The use of "N" in a primer denotes that those positions are degenerate.

A "specific region" (in contrast to a "3' target specific region" which is a broader genus) is able to bind to a transcriptome sequence occurring in a transcriptome with a frequency. In some embodiments, this frequency is between about 0.01% and 2.0%, such as, for example, between about 0.05% and 0.1% or between about 0.1% and 0.5%. In some embodiments, the length of the "specific region" of a primer depends mainly on the averaged lengths of the predicted PCR products based on bioinformatic calculations. The definition includes, without limitation, a "specific region" of between about 4 and 12 bases in length. In more particular embodiments, the length of the 3' specific region can, for example, be between about 4 and 20 bases, or between about 8 and 15 bases. Specific regions having a Tm of between about 10° C. and 60° C. are included within the definition. The term, "specific primer," when used herein refers to a primer of specified sequence.

The term "random region" as used herein refers to a region of an oligonucleotide primer that is able to anneal to unspecified sites in a group of target sequences, such as in a transcriptome. The "random region" facilitates binding of the primer to target mRNA. The random region nucleotides can be degenerate or non-specific, promiscuous nucleobases or nucleobase analogs. The length of the "random region" of the oligonucleotide primer, among other things, depends on the length of the specific region. In certain embodiments, without limitation, the "random region" is between about 2 and 15 bases in length, between about 4 and 12 bases in length or between about 4 and 6 bases in length. In another embodiment, the specific and random regions combined will be about 9 bases in length, e.g., if the specific region has 4 bases, the random region will have 5 bases.

In some embodiments, the 3' target-specific portion comprises both a specific region and a random region or degenerate region. In other embodiments, the 3' target-specific portion includes a specific region, and a random region or a degenerate region. In other embodiments, the 3' target specific region of the target primer only includes a specific region, a random region, or a degenerate region. Of course, known regions (sequences that are known) can also be used or part of the options disclosed herein.

In some embodiments, the 3' target-specific portion comprises a known nucleic acid sequence. Examples of known sequences can include poly-thymine regions and/or sequences that are complementary to splice sites in the target sequence (e.g., 5' (A/C)AGG3'). As used herein, a "/" separating two nucleotides denotes that either nucleotide can be employed. Thus, 5' (A/C)AGG3' denotes both 5'AAGG3' and 5'CAGG3'. A poly-thymine region can include 4 or more thymines, for example, 5, 6, 7, 8, 9, 10, 11, 12, 13, 14, 15, 16, or more thymines. In some embodiments, the 3' target-specific portion can comprise both a known region and a degenerate or random region. Such degenerate regions can be denoted by one or more "N". In some embodiments, the 3' target-specific portion can comprise both a known region, such as a poly-thymine region or a splice site, and one or more known alternative nucleotides, such as 1, 2, 3, 4, 5 or more adenine, guanine, and/or cytosine. In some embodiments, while it is known that the 3' target-specific region includes a poly-thymine region, the precise number of thymines does not need to be known, or can be varied. Of course, the term "known" does not require that one be aware of the fact that any specific primer is hybridizing to a target. Rather, the term is simply denoting a distinction between degenerate primers and primers with a definite sequence.

In some embodiments, the term "universal region," "universal primer region," or "universal priming region" as used herein refers to a region of an oligonucleotide primer that is designed to have no significant homology to any segment in the transcriptome. However, given that a noncomplementary region can be included in the target primer, nonspecific priming can be further reduced; thus, a universal region is not necessarily required for all embodiments. In some embodiments, the universal region is a region that allows for priming with a known primer. In some embodiments, this primer is common to at least one other nucleic acid sequences. In some embodiments, the "universal region" meets all the requirements for a normal oligonucleotide primer, such as lack of secondary structure, an appropriate Tm, and an appropriate GC content and can be between about 12 and 35 bases in length, between about 15 and 25 bases in length or between about 18 and 22 bases in length. However, as will be appreciated by one of skill in the art, the universal region, when part of the target primer, will be part of a larger structure. Additionally, because the universal region will be part of a larger primer, the universal region need only function as part of the entire target primer. As such, in these embodiments, the universal region need only assist in priming, as described in detail below. In some embodiments, the universal region functions independently as a priming site. In some embodiments, the universal region is the same as the noncomplementary region or they share some of the same nucleic acid sequences. "Universal priming site" when used herein refers to a "universal region" of a primer that can function as a site to which universal primers anneal for priming of further cycles of DNA amplification. In some embodiments, the target primer includes a universal region. The term "universal primer" as used herein refers to a primer that consists essentially of a "universal region". However, in some embodiments larger primers can comprise a universal region.

As used herein, the "noncomplementary region" refers to a nucleic acid sequence in a target primer or product thereof. The noncomplementary region is optional. The non-complementary region can reduce primer dimer formation. The noncomplementary region will include a sequence that is generally absent from the transcriptome. In some embodiments, oligo dTs can be used as the non complementary region and can reduce the number of Ts needed in the reverse transcription reaction. In addition, the oligo dT of the noncomplementary region can also be part included in the second primer used for second strand formation. In some embodiments, the noncomplementary region is a sequence that is present in at least some of the various primers or sequences in a reaction mixture. In some embodiments, the sequence is common in all or less than all of the primers used, for example 100, 100-99, 99-95, 95-90, 90-80, 80-70, 70-60, 60-50, 50-40, 40-30, 30-20, 20-10, 10-5, 5-1, 1% or less. Thus, in some embodiments, the primers for the target amplification all contain the same noncomplementary sequence. In some embodiments, the primers in subsequent steps (or a percent as noted above) also have the same noncomplementary region. As will be appreciated by one of skill in the art, the presence of similar sequences across various primers will reduce the likelihood that primer dimerization will occur (as the primers will be less likely to hybridize to one another). In some embodiments, the noncomplementary region is noncomplementary with respect to sequences in the target nucleic acid sequence. This embodiment is described in more detail below. In some embodiments, the noncomplementary region is both present in various primers (thereby reducing primer dimerization) and noncomplementary to sequences in the target sequences (e.g., a relatively long series of thymines).

The presence of the noncomplementary sequence need not absolutely prevent the occurrence of primer dimerization or other forms of nonspecific hybridization in every situation. In some embodiments, the presence of the noncomplementary region reduces the likelihood of these undesired forms of hybridization from occurring. In some embodiments, any decrease is sufficient, for example, less than 100% of the dimers that would have occurred without the noncomplementary region, e.g., 100-99, 99-98, 98-,95, 95-90, 90-80, 80-70, 70-60, 60-50, 50-40, 40-30, 30-20, 20-10, 10-5, 5-1, or less of the original primer dimers will occur when the noncomplementary region is present in the target primer. In some embodiments, the presence of the noncomplementary region decreases likelihood of nonspecific amplification or amplification of undesirably small sections of target nucleic acid sequence. Additionally, while the noncomplementary sequences can be the same in all of the primers or target primers used, they need not be the same. For example, in some embodiments, the noncomplementary regions, while not hybridizing, are not the same sequences (e.g., TTTT vs. CCCC) in different primers. In other embodiments, the noncomplementary regions are similar, but not identical, (e.g., TTTT vs. TTTC). In other embodiments, the noncomplementary regions are completely different types or sequences of nucleic acids; however, they will still reduce the likelihood of various forms of nonspecific hybridization. As will be appreciated by one of skill in the art, the length of the noncomplementary region can vary and the length required can depend on the various reaction conditions and the sequences present in the target sample, issues that can readily be determined by one of skill in the art.

In some embodiments, the noncomplementary region is effective at reducing the nonspecific hybridization of an amplification primer. The amplification primer can have a region that hybridizes to the noncomplementary region (as well as a region that can hybridize to the universal region). Thus, the amplification primer can be more specific for the double-extended target primer products rather than other nonspecific priming events that could occur if the amplification primer only contained a universal region. Thus, in some embodiments, the presence of a noncomplementary region in the target primer can assist in reducing subsequent nonspecific amplification.

In some embodiments, the noncomplementary region is at least 7-15 nucleotides in length. In some embodiments, the noncomplementary region comprises a series of thymine nucleotides. In some embodiments, the noncomplementary region is 8-12 thymines. In some embodiments, the noncomplementary region only includes 5, 6, 7, 8, 9, 10, 11, 12, 13, 14, 15, 16, 17, 18, 19, or 20 thymines (T), adenines (A), or similar nucleotides (such as artificial nucleotides). In some embodiments, the noncomplementary region is a series of thymines (0-10 nucleotides). In some embodiments, there is no noncomplementary region present in the primer or methods.

In some embodiments, the target primer does not include a noncomplementary region.

Figure 3:
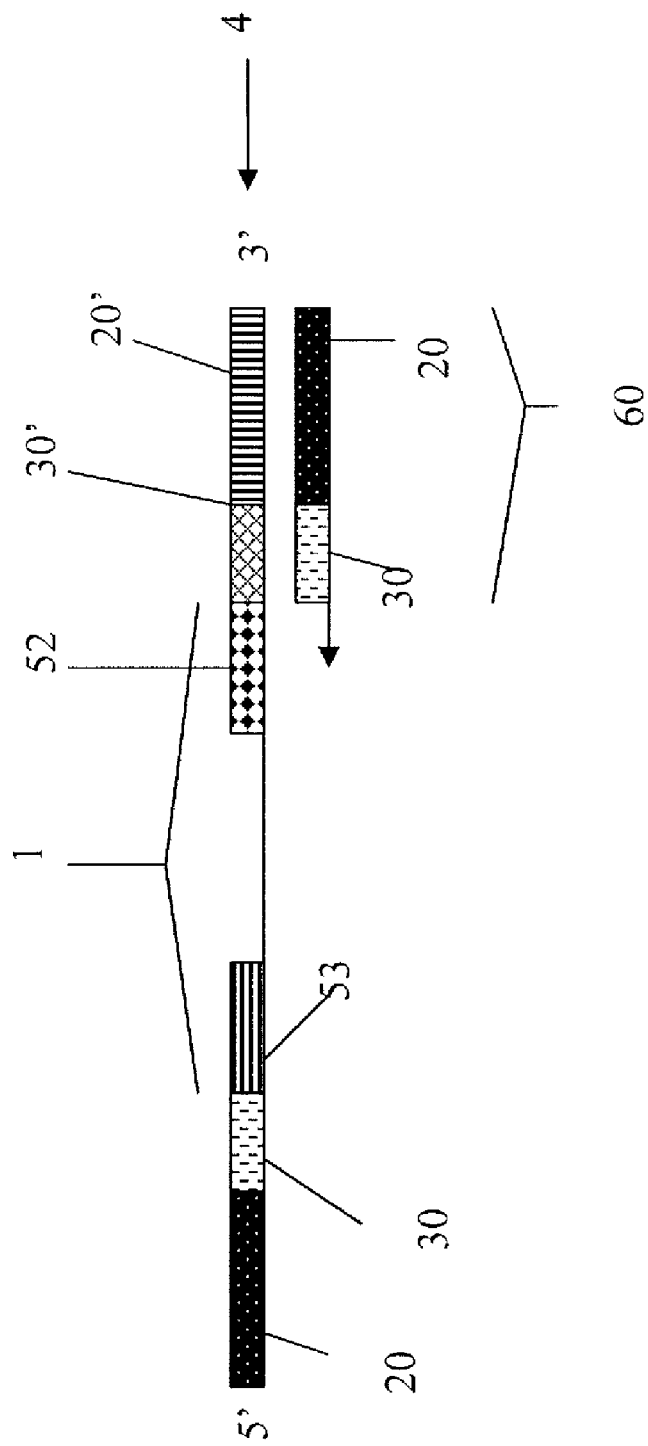
FIG. 3 depicts an embodiment of using a target primer.
Figure 4:
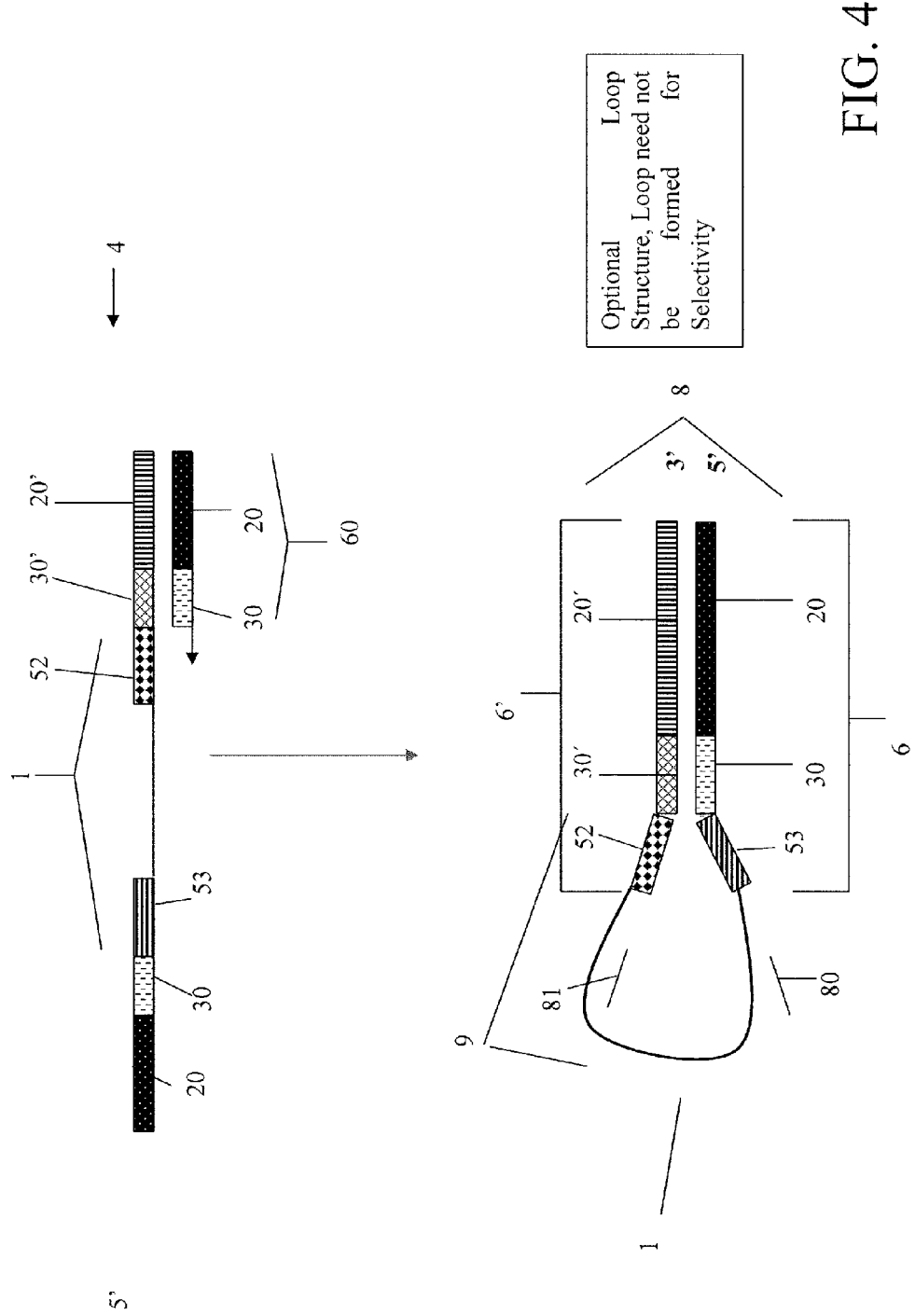
FIG. 4 depicts an embodiment of using a target primer.

As will be appreciated by one of skill in the art, while the term "noncomplementary" can denote that the sequence does not significantly or functionally complement another sequence in a mixture, there will be sequences that can hybridize to the noncomplementary region. For example, in a double-extended target primer (FIG. 3) there is both the target primer and the target primer complement (of course, as the target primer and the target primer complement can include random regions, they need not be 100% complementary at the 3' end, as shown in FIG. 4). Additionally, as noted above, in some embodiments, the amplification primer can also include a sequence that can hybridize to the noncomplementary region.

The term "does not effectively hybridize" denotes that the amount of hybridization that occurs is such that a significant reduction in primer dimerization or other forms of nonspecific hybridization occurs.

As used herein, the "target binding site" refers to a nucleic acid sequence, in the target nucleic acid sequence, where the 3' target-specific portion of the target primer can or is configured to hybridize to. As will be appreciated by one of skill in the art, this section can be part of the target nucleic acid sequence and can therefore be mRNA or other nucleic acid sequences.

As used herein, the "extended target primer" refers to a nucleic acid sequence that has been extended from a target primer hybridized to a target binding site. The extended target primer can include the target primer, along with a sequence that is effectively complementary to a sequence that is contained within the target sequence. In some embodiments, the extended portion of the extended target primer (that is to become the longer double-extended linear primer) is at least 100 nucleotides in length. In some embodiments, this extended portion is at least 200 nucleotides in length. In some embodiments, this extended portion is not more than 10 kb in length. As will be appreciated by one of skill in the art, those double-extended linear primers that are to become the shorter double extended linear primer can be shorter than the above ranges. In addition, in some embodiments, other lengths are contemplated. As will be appreciated by one of skill in the art, the "extended target primer" will include a target primer; however, it will not need to serve as a primer itself.

As used herein, the "target primer complement" refers to a nucleic acid sequence that is the complement of the target primer (of course, the target primer complement need not be 100% complementary, as the primers can include degenerate or random regions). As will be appreciated by one of skill in the art, in some embodiments, the sequence of the target primer complement can still form a looped primer itself. Additionally, any universal region and/or noncomplementary region in the target primer complement will be complementary to the relevant section in the target primer. An example of a target primer complement can be found in FIG. 3, on the right hand side of sequence 4, including sections 20', 30', and 52. However, as noted above, a target primer complement need not have a complementary 3' target specific region to the 3' target specific region in the target primer (as these can be from different initial target primers).

As used herein, the "universal region complement" refers to a nucleic acid sequence that is the complement of the sequence in the universal region.

The term "double-extended target primer" refers to a nucleic acid sequence that has been formed by extending a target primer that is hybridized to an extended target primer. In other words, the nucleic acid sequence has been extended twice via target primers. In some embodiments, the term "double extended target primer" simply means that there is a nucleic acid sequence that includes a target primer, a target sequence, and a target primer complement; the method by which it is made is not relevant. In some embodiments, the term "double extended target primer" simply means that there is a nucleic acid sequence that includes a universal region, a target sequence, and a universal region complement; the method by which it is made is not relevant. As will be appreciated by one of skill in the art, the "double-extended target primer" can include a target primer and a target primer complement (or just a universal region and a universal region complement); however, it does not necessarily need to serve as a primer itself.

The "amplification primer" can be used for amplifying the double extended target primer. An example of such a primer is depicted in FIG. 3, as 60. In some embodiments, the amplification primer comprises or consists of the universal region 20. In some embodiments, the amplification primer comprises or consists of the universal region 20 and/or a non-complementary region 30. In some embodiments, the amplification primer is a second target primer. In some embodiments, the amplification primer is not complementary to a first target primer. In some embodiments, the amplification primer has at least some of the same sequence as the target primer. In some embodiments, the amplification primer includes a sequence that is the same as the noncomplementary region. In some embodiments, the amplification primer includes a sequence that is the same as the universal region. As will be appreciated by one of skill in the art, the sequences need not be identical in all embodiments, as sequences that still selectively hybridize to the desired location can be employed as well. In some embodiments, the amplification primer is between 10-40 nucleotides long, such as a 30-mer. In some embodiments the amplification primer is 14 nucleotides long. In some embodiments, the amplification primer includes a "universal reverse primer," which indicates that the sequence of the reverse primer can be used in a plurality of different reactions querying different target nucleic acid sequences, but that the amplification primer nonetheless can be the same sequence. In some embodiments, the amplification primer includes a tail region that is not complementary to the sequence that the rest of the primer hybridizes to.

The term "insert section," "insert," "capture section," or "target section" refers to the section from one 3' target specific region to a second 3' target specific region, as shown in FIG. 4. In some embodiments, the insert section includes the 3' target specific region as well; thus, the insert section includes 52 and 53 in FIG. 4, and is defined between 20 and 20' and optionally 30 and 30'. As will be appreciated by one of skill in the art, in some embodiments, the insert section 9 can be looped, such as by the hybridization of the universal region and the universal region complement in a double-extended primer 8, as shown in FIG. 4, (e.g., the loop formed by the self-hybridization of the double-extended linear primer). However, in other embodiments, the insert section is not actually looped during various amplification steps (although they will be looped for the shorter insert sections, such as primer dimers, that are not to be amplified). As described in more detail below, even when not part of a looped structure, the length of the insert section or target section can still influence the amplification of the section. For example, shorter length insert sections will result in closer to zero order reaction kinetics between the universal region and its complement, while longer insert sections will increase the distance between the universal region and its complement, resulting in slower reaction kinetics. Thus, double extended target primers need not be looped in order to allow for selective amplification of longer insert sections over shorter insert sections. As will be appreciated by one of skill in the art, one can characterize the insert section as including some of the target primer sequence. Unless otherwise stated, "insert section" will include the region to which the target primer initially binds. Thus, a double extended target primer that is only a primer dimer, even if it includes nothing more than the random region of the linear primer, can still be characterized as "having" an insert section that is shorter than another double extended target primer. That is, an "insert section" does not have to include any target (or foreign) nucleic acid sequence and can simply be one or two random regions from the target primers.

Figure 5:
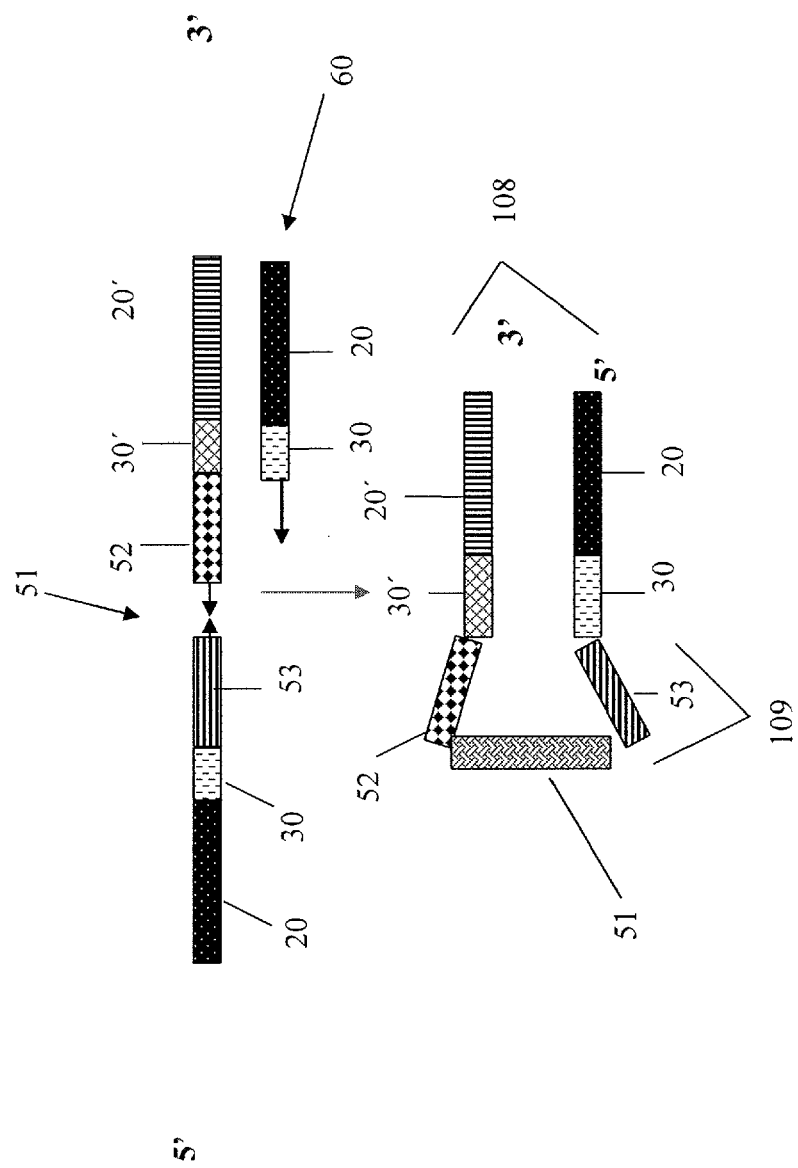
FIG. 5 depicts an embodiment of using a target primer.

In some embodiments, the insert section 9 can include a significant portion of target nucleic acid sequence, as shown in FIG. 4, which can then be amplified. Alternatively, the insert section can contain an insignificant amount of target DNA 51 (such as when primer dimers occur or overly frequent priming occurs), such an embodiment is shown in FIG. 5. In some embodiments, the insignificant amount of DNA 51 will be no DNA, as such, the insert section is only 53 connected to 52. In other embodiments, a small amount of the target nucleic acid sequence in included 51. In some embodiments, the insert section for the double-extended target primer to be amplified is between 100 by and 20 kb nucleotides in length.

The "capture stem" or "insert stem" denotes the section of the double-extended target primer that is self-hybridized. As will be appreciated by one of skill in the art, when the double extended target primer is simply a primer dimer, without any additional target nucleic acid sequence, the insert section will comprise the original linear primer sequences. As the structure can still be looped, there can still be unpaired nucleotides within the loop (although there need not be). Such primer dimer formations can be characterized as having an "empty insert section" or "no insert section", as they contain no additional sequence, apart from the starting primers. Alternatively, such primer dimer formations can be characterized as having "no foreign insert section", as they contain no additional sequence, apart from the starting primers; however, as they will still include the 3' target specific regions, there can still be a sequence within the insert section, even though none of it is foreign The term "insert amplification primer" or "insert primer" refers to a primer that can be used to amplify the insert section. Generally, these primers are complementary to some section of the target nucleic acid sequence that is within the double-extended target primer. In some embodiments, the insert amplification primers are specific primers with known or knowable sequences. In some embodiments, numerous insert amplification primers will be employed as the specific sequence that has been amplified may not be known. In some embodiments, two or more insert amplification primers are used to amplify the insert sections. In some embodiments, each insert amplification primer (or paired set thereof) will be combined with the double-extended target primer in a separate reaction chamber (thus the amplified double-extended target primer will be divided between numerous reaction chambers). In other embodiments, the numerous insert amplification primers and the amplification reaction are performed in a single reaction chamber or are combined in some manner. In some embodiments, the insert amplification primers are degenerate primers. In some embodiments, the insert amplification primers are relatively short to allow for ease of amplification. In some embodiments, the insert amplification primers include universal bases.

The term "intramolecular hybridization" refers to an event or state in which at least a portion of a nucleic acid strand is hybridized to itself.

The terms "self-hybridizing" or "self-hybridized" refer to an event or state in which a portion of a nucleic acid strand is hybridized to another portion of itself. In general, the term is reserved for the effective hybridization of the universal region of the target primer to at least a portion of the universal region complement (which can be within a target primer complement) in a double extended target primer, e.g., as shown in FIG. 5. For example the universal region can be hybridized to the universal region complement.

The term "large enough to allow amplification" in reference to the insert section (or looped target section) denotes that, relative to other species of sequences in the reaction mixture, the larger size of the insert of the described species allows for greater or more efficient amplification. If an insert has a "significant portion of target DNA" it will be large enough to allow amplification. In some embodiments, the insert is between 200 by and 10 kb or more nucleic acids in length. In some embodiments, the relative prevention is between a primer dimer (which comprises only the sequence of the target primer, e.g., a primer dimer) and a double extended target primer that includes at least one nucleotide in addition to the target primer.

The term "short enough to reduce the likelihood that amplification will occur" in reference to the insert section denotes that, relative to other species of sequences in the reaction mixture, the smaller size of the insert of the described species results in less and/or less efficient amplification compared to another species in the reaction mixture. If an insert has "an insignificant amount of target DNA" it is small enough to prevent or reduce the likelihood of amplification of the insert. In some embodiments, an insert that is short enough to reduce the likelihood that amplification will occur is between 1 and 200 nucleotides in length. In some embodiments, an insignificant amount of target DNA is from 1 to 200 nucleotides in length. As will be appreciated by one of skill in the art, as the target primer and primer complement can include a 3' target specific region some amount of the sequence of the target nucleic acid can appear to be present, even in situations where simple primer dimerization has occurred (and thus no target has been incorporated into the structure). In some embodiments, the above two terms are defined relative to one another. As will be appreciated by one of skill in the art in light of the present disclosure, in some embodiments the size of the looped target section (or insert section) is being used to preferentially reduce the amplification of smaller regions of the target nucleic acid sequence compared to larger target nucleic acid sequences. Thus, in some embodiments, the "prevention" or "reduction" of the amplification of a first double-extended target primer over a second double-extended target primer results from the fact that the first has a shorter insert section compared to the second. In some embodiments, any difference in size of the insert section can result in the desired "reduction" or selective amplification, for example, the insert section in a first double extended primer can be 99-90, 90-80, 80-70, 70-60, 60-50, 50-40, 40-30, 30-20, 20-10, 10-5, 5-1, 1-0.1, 0.1-0.001% or less the size of the insert section in the second double-extended target primer. In some embodiments, the prevention or reduction is specific to the prevention of the amplification of primer dimers. In such embodiments, the insert section is included in the primer portions, as these are the only portions that make up the entire structure. As will be appreciated by one of skill in the art, for primer dimers, the insert section is part of the primers themselves, as no additional sequence need be added. Thus, in such embodiments, the insert section overlaps with the 3' target specific region, the noncomplementary region, and/or the universal region. The insert section itself simply denotes the part that connects one primer to a previously separate primer, and can be part of one of the original primer sequences (e.g., the 3' target specific region, the noncomplementary region and/or the universal region). In some embodiments, primer dimers (structures that result from two primers hybridizing to one another and being extended) "include" an insert short enough to reduce the likelihood of amplification. Thus, in some embodiments, primer dimers will be removed from subsequent amplification. In some embodiments, the insert section in a primer dimer will not be large enough to allow amplification of the structure or the looped section in the primer.

In some embodiments, relative prevention is between designated larger and smaller sections. In some embodiments, the relative prevention or reduction in likelihood is in comparison to the same sequence as the insert sequence, except that the sequence is not looped (e.g., same insert sections sequence, but no or insignificant amounts of the stem forming region). In some embodiments, the relative prevention is between a primer dimer (which comprises only the sequence of the target primer, e.g., a primer dimer) and a double extended target primer that includes at least one nucleotide in addition to the target primer.

As will be appreciated by one of skill in the art, in embodiments in which one is amplifying within a self-hybridized structure, at large enough lengths, the amplification in the insert section does not change significantly upon increasing the length of the nucleic acid sequence in the insert section. However, these sequences can still be preferentially amplified over double-extended target primers having shorter length insert sections. As noted below, in some embodiments, insert sections of at least 100 by are generally used in order to have amplification in the loop. In embodiments in which SNP genotyping and gene dosage RT-PCR are employed, the length of the loops can be 100 by or longer, in order to allow spacing for two primers and probes (e.g., TAQMAN® probes). For some embodiments, such as capillary electrophoresis for sequencing applications, the insert sections can be 500 by or longer. Insert sections of at least 500 by can result in very efficient amplification in the loop. If longer loops are desired, the annealing time and/or extension time can be increased during PCR. In embodiments in which a self-hybridized structure is not formed for the longer double extended linear primer, then there need be no minimal size, as long as it is longer than the other double extended linear primer that the long double extended linear primer is to be amplified over.

As used herein, the term "identifying portion" refers to a moiety or moieties that can be used to identify a particular target primer species, and can refer to a variety of distinguishable moieties including zip codes, a known number of nucleobases, and combinations thereof. In some embodiments, an identifying portion, or an identifying portion complement, can hybridize to a detector probe, thereby allowing detection of a target nucleic acid sequence in a decoding reaction. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion and target nucleic acid sequence to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092).

Typically, identifying portions and their corresponding identifying portion complements are selected to minimize: internal, self-hybridization; cross-hybridization with different identifying portion species, nucleotide sequences in a reaction composition, including but not limited to mRNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

In some embodiments, the detector probe can hybridize to both the identifying portion as well as sequence corresponding to the target nucleic acid sequence. In some embodiments, at least two identifying portion-identifying portion complement duplexes have melting temperatures that fall within a $\Delta T_m$ range ($T_{max}$-$T_{min}$) of no more than 10° C. of each other. In some embodiments, at least two identifying portion-identifying portion complement duplexes have melting temperatures that fall within a $\Delta T_m$ range of 5° C. or less of each other. In some embodiments, at least two identifying portion-identifying portion complement duplexes have melting temperatures that fall within a $\Delta T_m$ range of 2° C. or less of each other.

In some embodiments, at least one identifying portion or at least one identifying portion complement is used to separate the element to which it is bound from at least one other component of a ligation reaction composition, a digestion reaction composition, an amplified ligation reaction composition, or the like. In some embodiments, identifying portions are used to attach at least one ligation product, at least one ligation product surrogate, or combinations thereof, to at least one substrate. In some embodiments, at least one ligation product, at least one ligation product surrogate, or combinations thereof, comprise the same identifying portion. Examples of separation approaches include but are not limited to, separating a multiplicity of different element-identifying portion species using the same identifying portion complement, tethering a multiplicity of different element-identifying portion species to a substrate comprising the same identifying portion complement, or both. In some embodiments, at least one identifying portion complement comprises at least one label, at least one mobility modifier, at least one label binding portion, or combinations thereof. In some embodiments, at least one identifying portion complement is annealed to at least one corresponding identifying portion and, subsequently, at least part of that identifying portion complement is released and detected, see for example Published P.C.T. Application WO04/4634 to Rosenblum et al., and Published P.C.T. Application WO01/92579 to Wenz et al.

As will be appreciated by one of skill in the art, while the presently disclosed target primers can include an identifying portion, it need not be included and is not included in some embodiments. In some embodiments, the target primer includes an identifying portion as well as the noncomplementary region. Is some embodiments, the identifying portion is not the same as the noncomplementary region. In some embodiments, an identifying portion is not included in a target primer.

As used herein, the term "extension reaction" refers to an elongation reaction in which the 3' target specific portion of a target primer is extended to form an extension reaction product comprising a strand complementary to a target nucleic acid sequence. In some embodiments, the target nucleic acid sequence is a mRNA molecule or fragment thereof. In some embodiments, the target nucleic acid sequence is a short DNA molecule and the extension reaction comprises a polymerase and results in the synthesis of a $2^{nd}$ strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different on a single double helix. For example, one PCR primer can directly hybridize to a first primer portion, while another PCR primer can hybridize to the complement of the second primer portion. In some embodiments, "universal" primers and primer portions as used herein are generally chosen to be as unique as possible given the particular assays and sequences involved to ensure specificity of the assay. However, as will be appreciated by one of skill in the art, when a noncomplementary region is employed, the need for uniqueness with regard to the universal region is greatly diminished if not removed completely.

Figure 7:
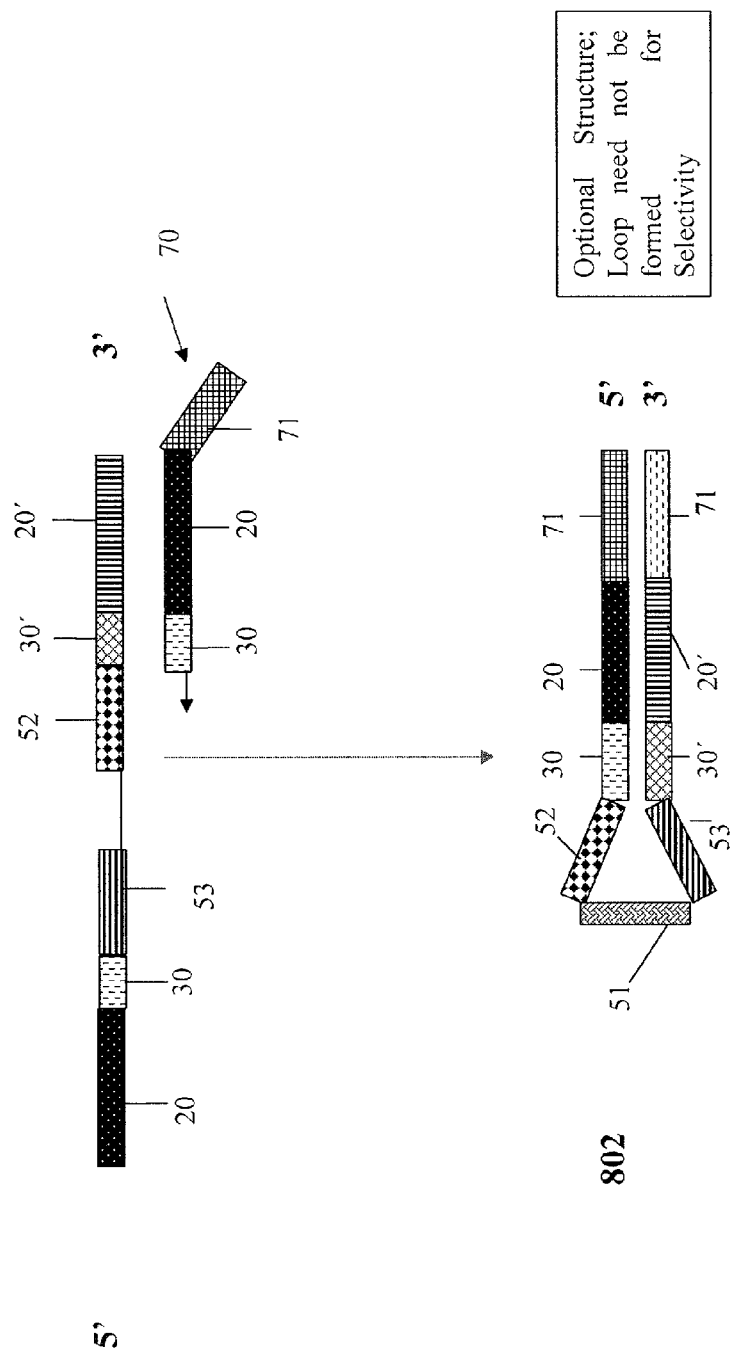
FIG. 7 depicts an embodiment of using a target primer.

The term "tail region" of a primer denotes a section at the 5' end of a primer sequence. In some embodiments this section can hybridize to part of a target sequence or priming site (e.g., such that the entire primer is hybridized to a target sequence or priming site). In some embodiments, the tail region has a sequence that is not complementary to the nucleic acid sequence that the remaining portion of the primer has hybridized to (e.g., the 5' end is not hybridized to a priming site while the rest of the primer can hybridize). In some embodiments, primers having different tail regions are used so as to allow for a sequence difference to be made at each end of the nucleic acid sequence (e.g., as shown in FIG. 7). Such a tail region can be denoted as a "noncomplementary tail region" or a second tail region, wherein the second tail region is different from the first. In some embodiments, the tail portion can include a zip-code, which can allow for the identification or tracking of the molecule associated with the zip-code. In some embodiments, the tail portion of the forward primer is between 5-8 nucleotides long. As will be appreciated by one of skill in the art, the length of the tail can determine the stability of the stem loop. If primer dimers are not a significant problem, the tail can be, for example, as large as a 20-mer to allow for the incorporation of forward and reverse primers for sequencing reactions that require two different primers. In some embodiments, one can reduce potential primer-dimer formation from carry over random primers by using tails that are less than 5-8 nucleotides in length. In some embodiments, a noncomplementary tail region is not used.

In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementarity, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings. Something is "configured to hybridize" when its sequence (e.g., structure) allows hybridization through base specific, e.g., A/T and G/C, by Watson/Crick and Hoogsteen-type hydrogen bonding.

As used herein, the term "amplifying" refers to any method by which at least a part of a target nucleic acid sequence, target nucleic acid sequence surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3.sup.rd Edition,; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol. Diagn. 2002 November; 2(6):542-8., Cook et al., J Microbiol Methods. 2003 May; 53(2):165-74, Schweitzer et al., Curr Opin Biotechnol. 2001 February; 12(1): 21-7, U.S. Pat. Nos. 5,830,711, 6,027,889, 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a target primer that is annealed to a template in the 5' to 3' direction using an amplifying means such as a polymerase and/or reverse transcriptase.

According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed target primer, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2).

In some embodiments of the present teachings, any of a variety of techniques can be employed prior to amplification in order to facilitate amplification success, as described for example in Radstrom et al., Mol. Biotechnol. 2004 February; 26(2):13346. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target nucleic acid sequence. In some embodiments, detector probes present in an amplification reaction are suitable for monitoring the amount of amplicon (s) produced as a function of time. Such detector probes include, but are not limited to, the 5'-exonuclease assay (TAQMAN®) probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor™ probes (U.S. Pat. No. 6,548,250), stem-loop and duplex Scorpion probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with $SO_3$ instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

The term "corresponding" as used herein refers to a specific relationship between the elements to which the term refers. Some non-limiting examples of corresponding include: a target primer can correspond with a target nucleic acid sequence, and vice versa. A forward primer can correspond with a target nucleic acid sequence, and vice versa. In some cases, the corresponding elements can be complementary. In some cases, the corresponding elements are not complementary to each other, but one element can be complementary to the complement of another element. When used with respect to two sequences (e.g., a target sequence and/or a sequence that "corresponds" to the target sequence) it denotes that the "corresponding" sequence is complementary to the target sequence. This can occur, for example, when the target sequence is used as a template for the creation of an extended target primer.

The term "or combinations thereof" as used herein refers to all permutations and combinations of the listed items preceding the term. For example, "A, B, C, or combinations thereof"

is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" or "reaction chamber" generally refers to any container in which a reaction can occur in accordance with the present teachings. In some embodiments, a reaction vessel can be an eppendorf tube or other container of the sort in common use in modern molecular biology laboratories. In some embodiments, a reaction vessel can be a well in a microtitre plate, a spot on a glass slide, or a well in an Applied Biosystems TaqMan Low Density Array for gene expression (formerly MicroCard™). A plurality of reaction vessels can reside on the same support. In some embodiments, lab-on-a-chip like devices, available for example from Caliper and Fluidgm, can provide for reaction vessels. In some embodiments, various microfluidic approaches as described in U.S. Provisional Application 60/545,674 to Wenz et al., can be employed. It will be recognized that a variety of reaction vessels are available in the art and within the scope of the present teachings.

As used herein, the term "detection" refers to a way of determining the presence and/or quantity and/or identity of a target nucleic acid sequence. In some embodiments the sequence to be detected is known. Thus, in some embodiments, detection occurs by determining if the target nucleic acid sequence comprises or consists of a known nucleic acid sequence, gene, etc. In some embodiments, the sequence to be detected is not known prior to the experiment. In such embodiments, the target nucleic acid sequence is amplified and sequenced. The sequencing of the target nucleic acid can be characterized as "detecting" the target nucleic acid. The target nucleic acid sequence to be sequenced can be known or unknown prior to its sequencing. Thus, in some embodiments, a target nucleic acid is sequenced to determine if a specific sequence or gene is present in a sample, and/or determine what specific variant is present. In some embodiments, a target nucleic acid is sequenced to determine the sequences of the genes or nucleic acid sequences themselves (e.g., the sequence and/or identity of the target nucleic acid sequence is not known prior to sequencing).

In some embodiments employing a donor moiety and signal moiety, one can use certain energy-transfer fluorescent dyes for detection. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, VIC®, LIZ®, TAMRA™ (carboxytetramethylrhodamine, succinimidyl ester), 5-FAM™ (5-carboxyfluorescein), 6-FAM™ (6-carboxyfluorescein), and Texas Red (Molecular Probes). (VIC®, LIZ®, TAMRA™, 5-FAM™, and 6-FAM™ all available from Applied Biosystems, Foster City, Calif.).

In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction does not need to take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification.

In some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid sequence. As used herein, determining the presence of a target can comprise identifying it, as well as optionally quantifying it. In some embodiments, the amplification products can be scored as positive or negative as soon as a given number of cycles is complete. In some embodiments, the results can be transmitted electronically directly to a database and tabulated. Thus, in some embodiments, large numbers of samples can be processed and analyzed with less time and labor when such an instrument is used.

In some embodiments, different detector probes can distinguish between different target nucleic acid sequences. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' can form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "5'-nuclease analysis" or "5'-nuclease assay" when used herein refers to "real-time analysis" for quantification of the amount of DNA amplified in a particular PCR reaction. TAQMAN® analysis is an example of such "5'-nuclease analysis" (a commercially available PCR kit). "5'-nuclease analysis" involves the use of a fluorogenic oligonucleotide probe to which a reporter dye and a quencher dye are attached. During amplification of a nucleotide sequence using a forward and reverse primer, the probe anneals to the target of interest between the forward and reverse primer sites. During extension, the probe is cleaved by the 5'-nuclease activity of the DNA polymerase. As the cleavage separates the reporter dye from the quencher dye, the reporter dye's fluorescence increases which can be detected and quantitated. Real-time analysis of PCR with 5'-nuclease assay involves FRET probes that can be displayed by plotting the logarithmic change in detected fluorescence ($\Delta Rn$) versus the cycle number. The cycle within the PCR protocol at which the change in fluorescence ($\Delta Rn$) rises above a threshold value is denoted as $C_T$. The $C_T$ cycle is approximately the cycle at which amplification of target becomes exponential. A relatively low $C_T$ value indicates efficient detection of amplicon. The threshold cycle is highly correlated to the amount of copy number, or amount of target nucleic acid sequence present in the sample, as well as the efficiency of amplification. The effects of primer constitution, e.g. length, sequence, mismatches, analogs, can be conveniently screened and quantitated by measurement of $C_T$ values during real-time analysis of PCR. In some embodiments, the sequences within the insert sections can be detected and/or amplified via a TAQMAN® assay or similar assay.

"Polymerase chain reaction" or "PCR" as used herein, refers to a method in the art for amplification of a nucleic acid. The method can involve introducing a molar excess of two or more extendable oligonucleotide primers to a reaction mixture comprising the desired target sequence(s), where the primers hybridize to opposite strands of the double stranded target sequence. The reaction mixture is subjected to a program of thermal cycling in the presence of a DNA polymerase, resulting in the amplification of the desired target sequence flanked by the oligonucleotide primers. The oligonucleotide primers prime multiple sequential rounds of DNA synthesis, each round of synthesis is typically separated by a melting and re-annealing step. Methods for a wide variety of PCR applications are widely known in the art, and are described in many sources, for example, Ausubel et al. (eds.), Current Protocols in Molecular Biology, Section 15, John Wiley & Sons, Inc., New York (1994).

"In silico PCR" when used herein refers to a computer-conducted method for predicting the size and probability of amplification of a nucleotide sequence using a particular set of primers. The method involves searching a DNA database for exact matches to the primer sequences and further for sequences having the correct order, orientation, and spacing to allow priming of amplification of a nucleotide sequence of a predicted size.

"Tm" as used herein, refers to the melting temperature (temperature at which 50% of the oligonucleotide is a duplex) of the oligonucleotide calculated using the nearest-neighbor thermodynamic values of Breslauer et al. (Proc. Natl. Acad. Sci. USA 83:3746 3750, 1986) for DNA and Freier et al. (Proc. Natl. Acad. Sci. USA 83:9373 9377, 1986) for RNA.

As will be appreciated by one of skill in the art, the above definitions occasionally describe various embodiments that can also be used, in some embodiments, with the variously defined parts or steps. Unless indicated, these various embodiments are not required or part of the actual definitions and have been included for additional general context and for further description of the various contemplated embodiments.

Aspects of the present teachings can be further understood in light of the following description and examples, which should not be construed as limiting the scope of the present teachings in any way.

Linear Primers

Figure 1B:
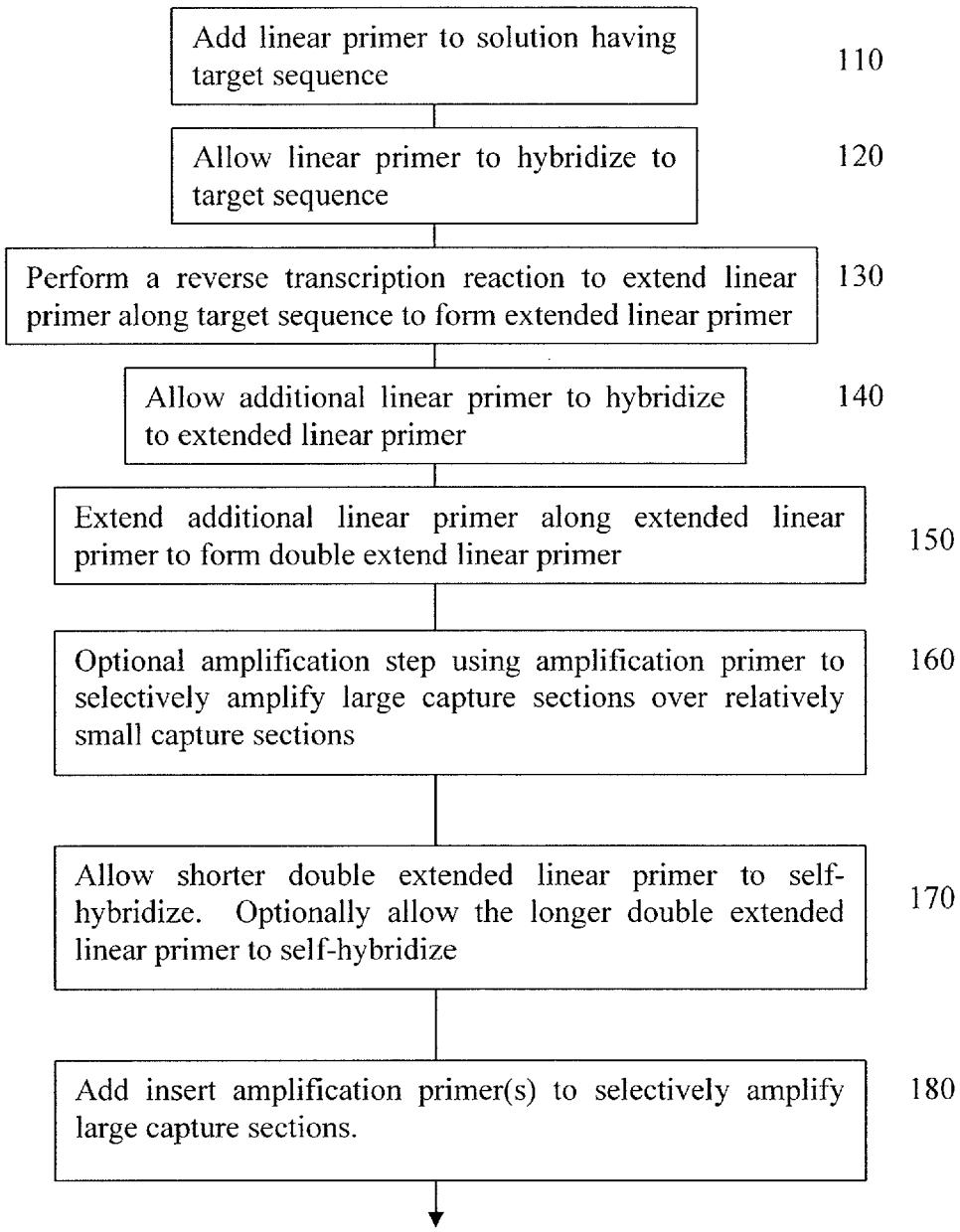
FIG. 1B is a flow chart depicting one embodiment using a linear target primer to produce a self-hybridizing nucleic acid sequence.
Figure 1C:
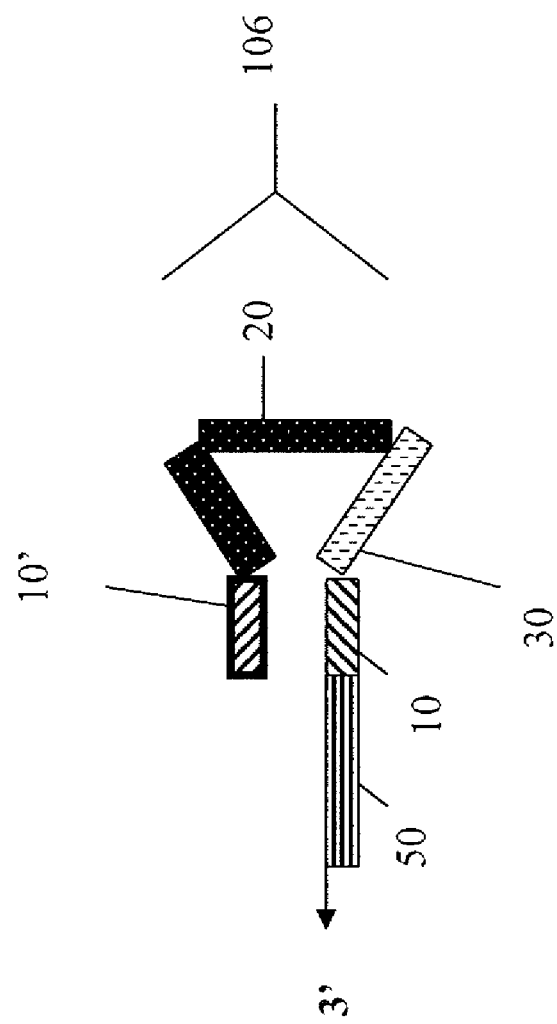
FIG. 1C depicts one embodiment of a loopable target primer.

FIGS. 1A and 1B depict one embodiment of a target primer, in particular a linear primer 6, and an embodiment of its use. The linear primer can include a 3' target specific region 50, a universal region 20, and optionally a noncomplementary region 30.

As described in detail below, and outlined in FIG. 1B, in some embodiments, the linear primer can be used to initiate priming as desired (e.g., via a random, specific, or degenerate priming region), while still including a universal and/or a noncomplementary region in the primer. Moreover, this can be achieved with a reduced risk of nonspecific or primer-dimer interactions occurring.

In some embodiments, such as the one depicted in FIG. 1B, the use of the linear primer to amplify sections of a target sequence allows one to place complementary sequences on either end of an insert corresponding to the amplified target nucleic acid sequence. As noted below, the addition of these complementary sequences allows for the selective amplification of the target nucleic acid sequences.

The first step depicted in FIG. 1B is the addition of a linear primer (6 depicted in FIG. 1A) to a solution that includes the target nucleic acid sequence or sequences that are to be amplified 110 or in which a target is to be identified, if present. Conditions are selected such that the linear primer hybridizes to the target sequence 120. The linear primer is then extended, via a reverse transcription reaction, along the target sequence to form an extended linear primer 130. One can then allow a linear primer (the same degenerate linear primer, an identical linear primer, or a different linear primer, as long as the same universal region is present) to hybridize to the extended linear primer 140. As outlined in more detail in the sections below, in some embodiments, the second linear primer can include a splice site specific region or a random region. Then one can extend the linear primer along the extended linear primer to form a double-extended linear primer 150. In various embodiments, the linear primers can have identical sequences; can have identical sequences apart from the 3' target specific region; can have different sequences, apart from the noncomplementary region; or can have different sequences.

In some embodiments, some or all of steps 110-150 can be repeated as desired. In some embodiments, some or all of steps 110-150 can be repeated as desired prior to proceeding to step 160. Following step 150, one can optionally amplify the double-extended linear primer using an amplification primer 160. The amplification primer will have a sequence that will hybridize to a sequence that is complementary to the universal region on the primer (e.g., the amplification primer can have a sequence that is or is a part of the universal region) and, optionally (if necessary), a sequence that will hybridize to a sequence that is complementary to the noncomplementary region (e.g., is or is part of the noncomplementary region). As will be appreciated by one of skill in the art, in some embodiments, only one of these regions will be present.

In some embodiments, one can then allow the shorter double-extended linear primer to self-hybridize 170. In some embodiments, one can allow both the short and the long double-extended linear primers to self-hybridize. This self-hybridized population can then be used in the amplification of large insert sections over relatively small insert sections 180 (depicted in FIGS. 1B and 1D). Thus, in some embodiments, the use of the linear primer described above results in a self-hybridized population that allows for the selective amplification of larger sections of target nucleic acid sequences over smaller sections of target nucleic acid sequences contained within the self-hybridized structures. In some embodiments an initial reverse transcription step can be performed or a cleaning step can be included, for example as described in the following sections.

While the self-hybridized structure can be used to help select larger insert section (or insert sections) over smaller insert sections, the larger double extended linear primer need not assume a looped configuration. For example, in some embodiments, the self-hybridized structure is only formed for the shorter insert sections. Thus, in some embodiments, selective amplification of longer insert sections over shorter insert sections (including primer dimers) occurs without the formation of a self-hybridized structure for the longer double extended linear primer. Without intending to be limited by theory, it is understood that because a shorter insert sections will mean that there is less distance between the linear primer and the linear primer complement, that these short double extended linear primers will self hybridize faster than double extended linear primers with larger insert sections. Similarly, the larger double-extended linear primers will have more distance between the linear primer and its complement and thus it can take longer for the primer and its complement to self-hybridize. Thus, in some embodiments, it is the faster ability of the double extended linear primers having shorter insert sections to self-hybridize, and thus take themselves out of a reaction, that allows for the selective amplification of the double extended linear primers having the longer insert sections over the shorter (or no foreign) insert sections. Thus, in some embodiments, the longer or long insert section is not in a looped configuration during the selective amplification.

Loopable Primers

FIG. 1C depicts one embodiment of a target primer 106, in particular a loopable primer. The loopable primer can include a 3' target specific region 50, a first loop-forming region 10, a second loop forming-region 10', a universal region 20 and, optionally, a noncomplementary region 30.

As described in detail below, and outlined in FIG. 1D, in some embodiments, the loopable primer can be used to initiate priming as desired (e.g., via a random or degenerate priming region), while still maintaining the ability to include a universal and a noncomplementary region in the primer. Moreover, this can be achieved with a reduced risk of nonspecific or primer-dimer interactions occurring.

Figure 1D:
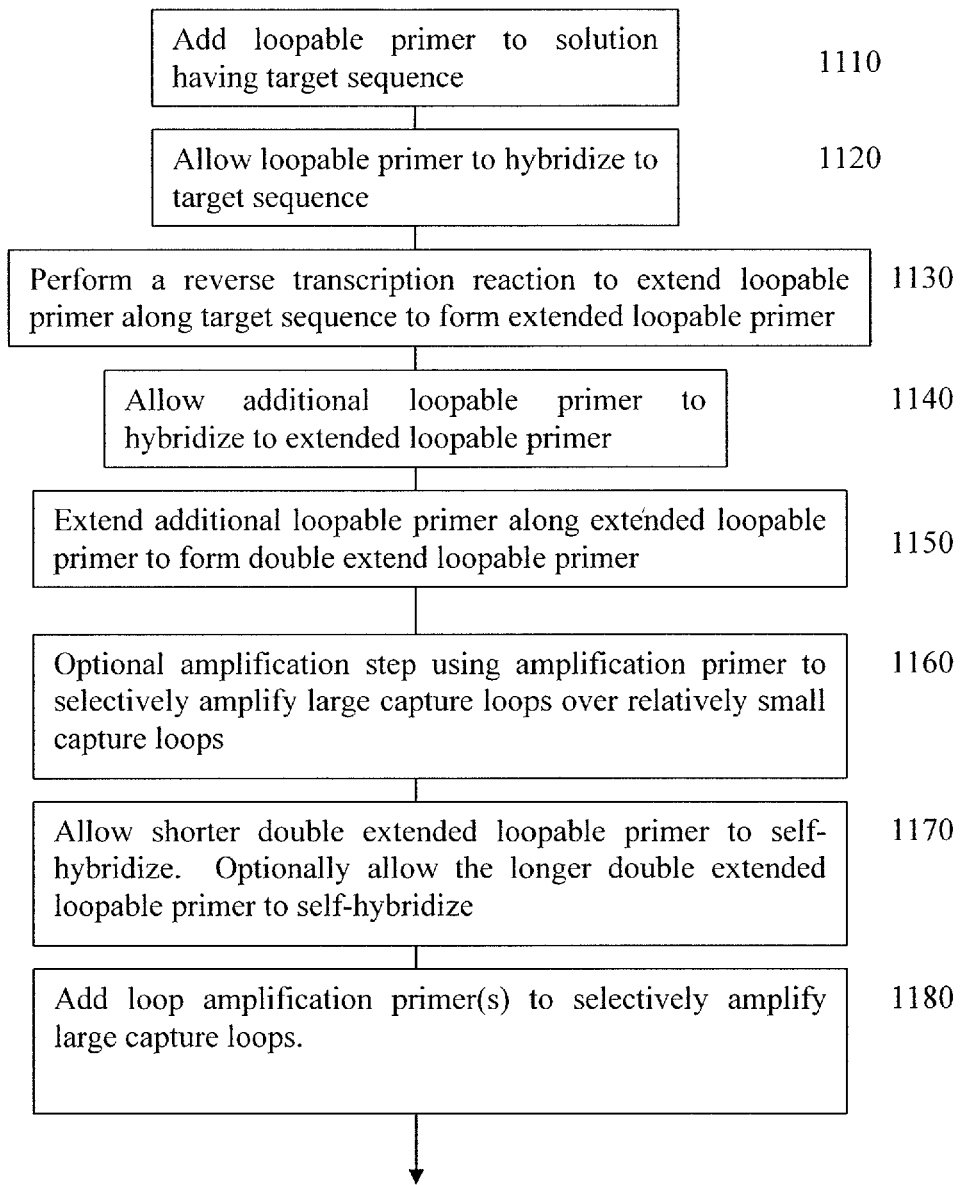
FIG. 1D is a flow chart depicting one embodiment using a loopable target primer to produce a self-hybridizing nucleic acid sequence.

In some embodiments, such as the one depicted in FIG. 1D, the use of the loopable primer to amplify sections of a target sequence allows one to place complementary sequences on either end of the amplified target nucleic acid sequence. As these sequences are complementary, they can hybridize together forming a looped structure (described as a self-hybridized double-extended loopable primer). As noted herein, subsequent amplification of the self-hybridized double-extended loopable primer will depend upon the size of the insert section. When relatively small sections (or no section) have been amplified, the presence and size of the insert will prevent further amplification, effectively removing or reducing the presence of these undesired species from the reaction mixture. This embodiment of the method is generally outlined in FIG. 1D.

The first step depicted in FIG. 1D is the addition of a loopable primer to a solution that includes the target nucleic acid sequence or sequences that are to be amplified 1110 or in which a target is to be identified, if present. Conditions are selected such that the loopable primer hybridizes to the target sequence 1120. The loopable primer is then extended, via a reverse transcription reaction, along the target sequence to form an extended loopable primer 1130. One can then allow a loopable primer (the same degenerate loopable primer, an identical loopable primer, or a different loopable primer, as long as the same universal region is present) to hybridize to the extended loopable primer 1140. As outlined in more detail in the sections below, in some embodiments, the second loopable primer can include a splice site specific region or a random region. Then one can extend the loopable primer along the extended loopable primer to form a double-extended loopable primer 1150. In various embodiments, the loopable primers can have identical sequences; can have identical sequences apart from the 3' target specific region; can have different sequences, apart from the noncomplementary region; or can have different sequences.

In some embodiments, some or all of steps 1110-1150 can be repeated as desired. In some embodiments, some or all of steps 1110-1150 can be repeated as desired prior to proceeding to step 1160.

Following the step 1150, one can optionally amplify the double-extended loopable primer using an amplification primer 1160. The amplification primer will have a sequence that will hybridize to the complement of the universal region (e.g., it will include a universal region sequence) and, optionally, a sequence that will hybridize to the complement of the noncomplementary region. In some embodiments, one can then allow the double-extended loopable primer to self-hybridize 1170. In some embodiments, the primer-dimers and other short length double-extended loopable primers more readily form the self-hybridized structures than the longer double-extended loopable primers, thereby effectively removing these structures from amplifications. On the other hand, longer double-extended loopable primers can take longer to self-hybridize, giving the amplification primer enough time to anneal and amplify these longer double-extended loopable primers. In some embodiments, the longer double-extended loopable primers are so long that even when self-hybridized, there is sufficient space as to allow amplification of the insert section. Thus, the self-hybridized structure (of at least the shorter insert section containing double-extended loopable primers) can then be used for the selective amplification of large insert sections over relatively small insert sections 1180 (depicted in FIGS. 4 and 5 with respect to linear primers). The use of the loopable primer described above results in a self-hybridized structure that allows for the selective amplification of larger sections of target nucleic acid sequences over smaller sections of target nucleic acid sequences contained within the self-hybridized structures. In some embodiments an initial reverse transcription step can be performed or a cleaning step can be included (or excluded), as described in the following sections. As will be appreciated by one of skill in the art, the reverse transcription step can produce a cDNA from the target nucleic acid.

The following sections describe additional various embodiments. While the figures generally depict linear primers as an example of the "target primer," one of skill in the art will understand that the descriptions (and relevant portions of the figures) apply equally to the loopable primers described above. Thus, the following embodiments apply and are meant to describe both linear and loopable primer embodiments (unless stated otherwise).

General Target Primer Uses and Embodiments

Figure 1E:
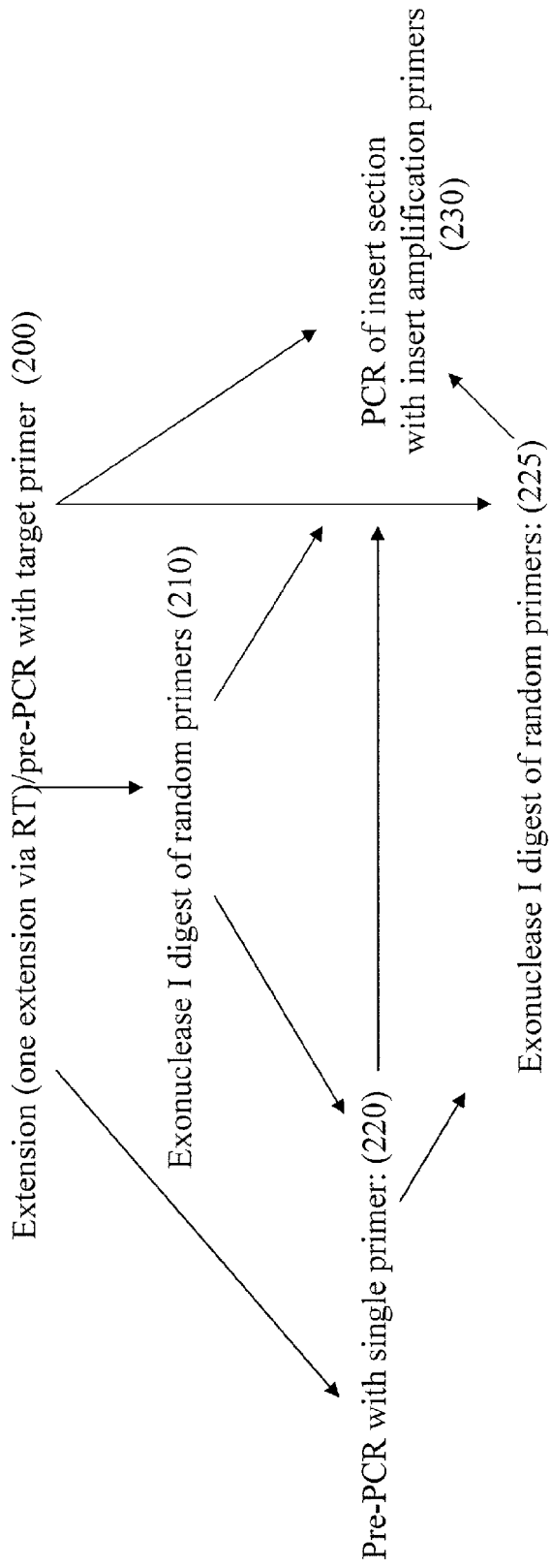
FIG. 1E is a flow chart depicting some embodiments involving a target primer.

Additional embodiments of the method of using the target primers for the selective amplification of relatively larger target nucleic acid sequences (compared to shorter target nucleic acid sequences) are shown generally in FIG. 1E. The first step 200 can involve primer extension via the target primers described above (e.g., using a reverse transcription reaction to form an extended target primer and extending from a second target primer to form a double-extended target primer) which can be followed by step 210, a digestion of various random primers, such as with exonuclease I. In some embodiments, this is followed by a pre-PCR amplification step with a single amplification primer (step 220). Following this, a step is performed to amplify the insert section, depending upon the size of the target nucleic acid sequence within the insert section. This can be achieved with an insert amplification primer (step 230). As shown in FIG. 1E by the arrows, various steps can be included or removed for various embodiments. In some embodiments, the cleaning step 225 is not performed or is performed after the pre-PCR amplification 220. In some embodiments, multiple rounds of cleaning (e.g., exonuclease digestion) are employed. Specific embodiments involved in these methods are discussed in more detail in regard to FIGS. 2-7.

Figure 2:
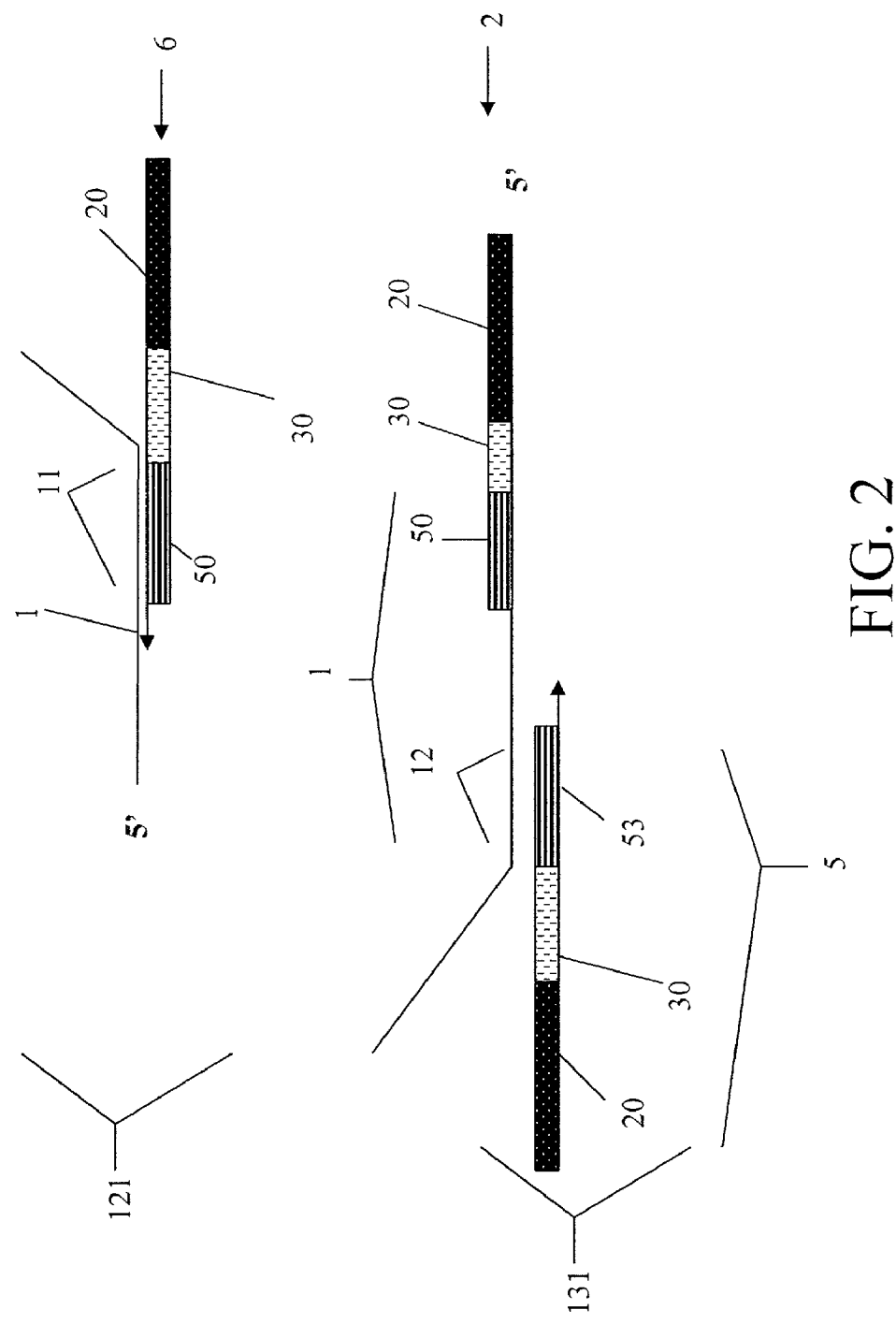
FIG. 2 depicts an embodiment of using a target primer.

In the top section of FIG. 2, the target primer 6 is shown hybridized at a first part 11 at a complementary portion of the target nucleic acid sequence 1 in a first arrangement 121. This results from a first step in which the target primer 6 is allowed to anneal via the 3' target specific region 50 to the first part of the target nucleic acid sequence at a target binding site 11. Following the hybridization, the primer is extended, via a reverse transcription reaction, along the target sequence in the 5' direction of the target sequence or in the 3' direction from the target primer (arrow). Following this extension, an additional target primer 5 (which can have the same sequence as the first target primer, a different sequence (but same universal region 20 and/or noncomplementary region 30), and/or a 3' target specific region 53 and/or universal region 20 and/or noncomplementary region 30, hybridizes at a complementary portion of the extended target primer 2 at a second target binding site 12, as shown in FIG. 2, in a second arrangement 131. The target primer 6 can include a 3' specific target region 53 (which can be random or specific, (for example, capable of hybridizing to a splice site sequence)), a noncomplementary region 30, and a universal region 20. In some embodiments, the target primers 5 and 6 are the same. In some embodiments, the target primers are the same, apart from their 3' target specific region 50 and 53. One of skill in the art will appreciate that various adjustments can be made, as long as the two primers can still hybridize as shown in FIGS. 4 and 5.

In some embodiments, the 3' target specific region is a degenerate region; thus, identifier "50" can represent multiple or different sequences on different primers as it can be a degenerate sequence. For FIGS. 2-7, the 3' target specific region is depicted as identifier 50 and 53, and thus the specific sequences of 50 and 53 are identified by different identifiers in the figures. However, both 50 and 53 can be a 3' target known or specific region (and thus can be the same in some embodiments) or a random or degenerate sequence. In addition, the 3' target specific region identifier "50" can be used generically throughout a single figure, to denote different sequences, even though a single identifier is used (thus, "50" and "52" and "53" need not be present to denote that a region is degenerate or different). One of skill in the art will readily appreciate how this and other sequences within these linear primers 5 & 6 can be differed, if desired.

Following the hybridization of the target primer 5 to the extended target primer 2 the target primer 5 is extended from its 3' direction to the 5' direction of the extended target primer. This extension results in a double-extended target primer 4

(FIG. 3). As noted above, the term "double-extended target primer" does not imply that the sequence functions as a primer, but that it is formed from extending target primers.

The double-extended target primer can optionally be amplified at this point. This is shown in more detail in FIG. 3 in which an amplification primer 60 is used to amplify the double-extended target primer 4. In some embodiments, the amplification primer comprises, consists, or consists essentially of the universal region 20. In some embodiments, the amplification primer includes the noncomplementary region 30 and a universal region 20. This amplification primer 60 can hybridize to the double-extended target primer allowing for efficient amplification of the double-extended target primer. In some embodiments, more than one amplification primer can be used. In some embodiments, only a single primer per target primer nucleic acid sequence is used in the amplification step depicted in FIG. 3. In some embodiments, the use of a single primer sequence that will not hybridize to the initial target primer can help reduce nonspecific primer dimerization that could otherwise occur due to the presence of an amplification primer and remaining target primers. Thus, by selecting an amplification primer that has the same sequence as a portion of the target primer, one can further reduce the risk of primer dimerization or other nondesired hybridization events. Of course, the presence of the noncomplementary region 30 in the target primer 6 can be exploited in selecting such an amplification primer 60. In some embodiments, the amplification of the double extended linear primer results in the selective amplification of double extended linear primers having long insert sections over those with shorter or no insert sections.

As will be appreciated by one of skill in the art, the amplification step can occur in situations in which additional background DNA, mRNA, or nucleic acid sequences are present. As will be appreciated by one of skill in the art, in embodiments in which the linear amplification primer only hybridizes to the universal region, there could be significant priming events to non target sections. However, the presence of the noncomplementary region in the target primer (and more specifically sequences complementary to these regions in the double-extended target primer) and in the amplification primer reduce the likelihood that this will occur.

Following the optional amplification step, at least a subpopulation of the double-extended target primer can self-hybridize (e.g., to achieve the configuration 108, as shown in FIG. 5). As noted above, self-hybridization of the double extended target primer does not have to occur for all species in a sample. Rather, self-hybridization need only occur for the shorter sequences (FIG. 5) which are to be reduced or amplified over. Thus, in some embodiments, self-hybridization occurs for the structures in FIG. 5, but not for the structures depicted in FIG. 4. However, in some embodiments, the longer double-extended target primers also self-hybridize, as shown in FIG. 4.

As will be appreciated by one of skill in the art, the portions of the double-extended target primer corresponding to the universal region 20 and the universal region complement 20' are capable of hybridizing to one another. The insert section 9 itself can then have the target nucleic acid sequence, or fragment thereof, which can be amplified (for example by PCR). In some embodiments, insert amplification primer(s) 80 and/or 81 are used to amplify at least a portion of the insert. As will be appreciated by one of skill in the art, the size of the insert can be sufficient to allow amplification.

In embodiments in which self-hybridization of the longer double extended target primers is not required to occur (e.g., does not occur frequently or is not driving a subsequent selective amplification of longer insert sections over shorter insert sections), then the selective amplification can occur due to the fact that the shorter double-extended target primers self-hybridize more rapidly than the longer double-extended target primers and thus are removed from subsequent rounds of amplification more quickly than the longer double-extended target primers. In such embodiments, while self-hybridization still occurs for the shorter double-extended target primers (e.g., primer dimers) it does not need to occur for the longer double-extended target primers. As the universal region of the target primer and the universal region complement of the target primer complement on these longer double-extended target primers (as depicted in FIG. 4) are separated by more nucleotides than the shorter double-extended target primer (FIG. 5), the self-hybridization of the longer double-extended target primers will take longer, allowing more time for the insert amplification primer to hybridize and extend. Thus, the self-hybridized structure for the longer double-extended target primer need not be formed to selectively amplify the longer double-extended target primer over the shorter double-extended target primer.

As will be appreciated by one of skill in the art, in embodiments in which whole transcriptome amplification is being performed, the precise sequence within the insert section can be unknown. In light of this, it can be advantageous to use multiple insert amplification primers to make certain that one will prime and extend as desired. In some embodiments, a pool of insert amplification primers is used. In other embodiments, one insert amplification primer (and/or one set or more) is mixed with the solution containing the double-extended target primer. As will be appreciated by one of skill in the art, numerous such mixtures (e.g., 2-10, 10-100, 100-1,000, 1,000-10,000 or more) can be done in series or in parallel. Furthermore, the solution containing the double-extended target primer can be divided into parts so that the various reactions can be run in parallel.

As will be appreciated by one of skill in the art, not every target primer will necessarily hybridize to the target sequence as desired and in some embodiments a target primer duplex or primer dimer will be formed. For example, in some situations, subsequent primers (such as an amplification primer) can hybridize to the target primer complement, resulting in only the amplification of the primer. Additionally, in some embodiments, target primers can hybridize to one another, also forming short amplification products. Additionally, in some embodiments, nonspecific hybridization or overly frequent hybridization of the 3' target specific region or of other sections (such as the universal region) of the various primers to sections of the target nucleic acid sequence can occur such that only these smaller sections of the target nucleic acid sequence are amplified. One depiction of the above is shown in FIG. 5. In such a situation, rather than having target nucleic acid sequence (or a significant amount of it) between the universal region 20 and the complement to the universal region 20', there is an insignificant amount of target sequence between the two 20 and 20'. As shown in FIG. 5, when the universal region 20 and universal region complement 20' hybridize together under this situation, the insert section 109 in the complex 108 is relatively small. In some embodiments, there is a nucleic acid sequence 51 in the insert section between the 3' target specific region 50 and 53. This nucleic acid sequence 51 need not be present and, if it is present, is relatively short. In some embodiments, (when a sufficiently large insert is present) the insert 9 (including sequence 51) is not more than 20 kb in length. In some embodiments, the insert 109, while still capable of allowing amplification does so with relatively less efficiency than the double-extended target primer complex 8 shown in FIG. 4 (which, of course, need not actually assume the structure shown during the process). As such, relative amplification of the product 8 (or 4 in the non-self-hybridized form) shown in FIG. 4 can be achieved compared to amplification of the resulting product 108 shown in FIG. 5. As will be appreciated by one of skill in the art, this distinction between the two resulting products can reduce the role or impact that nonspecific primer interactions can have. That is, this distinction can generally improve target detection or sequence amplification by reducing the impact of nucleic acid structures (or products) in which a significant or substantial amount of target RNA has not incorporated between the two primers. As will be appreciated by one of skill in the art, when the 3' target specific regions 52 and 53 are complementary to one another (e.g., when only a single sequence is used and the 3' target specific region is not a degenerate sequence) the complement 53 can be hybridized together and the sequence 51 need not be present (e.g., when the double-extended target primer is just a primer dimer). In embodiments in which the 3' target specific region is a degenerate region or sequence, then sections 52 and 53 need not, and often will not, be complementary to one another.

While not depicted in FIGS. 4 and 5, one of skill in the art will readily recognize that in the embodiments in which a self-hybridized structure is not created for the longer double-extended linear primer, that the insert amplification primers 81 and 80 can bind to the "open" double-extended linear primer, and can bind to the universal region or other section of the linear primer. In some embodiments, one of the insert amplification primers comprises, consists, or consists essentially of a universal region, while the second insert amplification primer primes in the insert. In some embodiments, both insert amplification primers hybridize within the insert (as shown in FIG. 4, although no actual loop need be formed). In some embodiments, neither of the insert amplification primers prime or overlap with any section of the linear primer.

Figure 6:
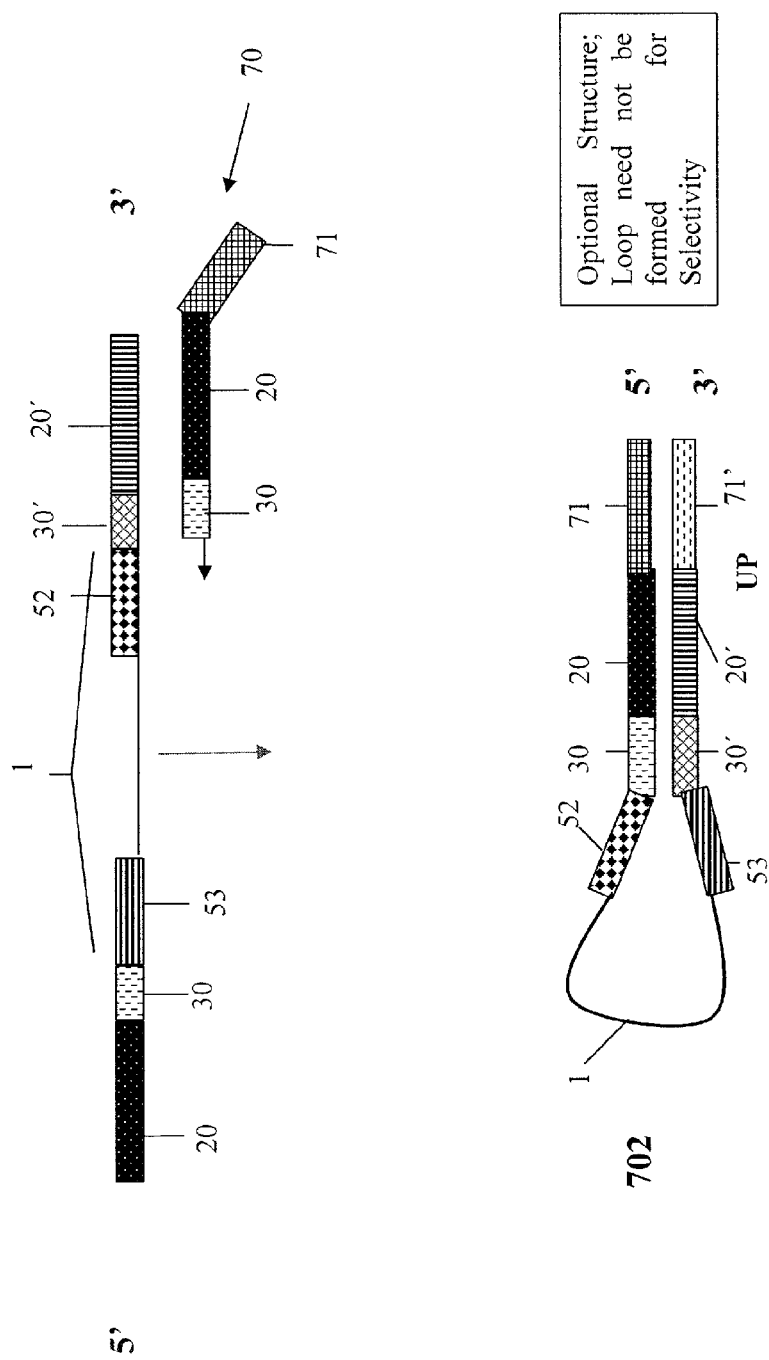
FIG. 6 depicts an embodiment of using a target primer.

As will be appreciated by one of skill in the art, in some embodiments, it is desirable to have specific sequences on the 5' and/or 3' end of the nucleic acid sequence that have been amplified, such as the double-extended target primer. Examples of such specific sequences include zip-code sequences, as described in U.S. Pat. Pub. No: 2006/0014191 (the entirety of which is hereby incorporated by reference). One option for achieving this is shown in FIG. 6 and FIG. 7 (which depict the self-hybridized embodiments only, although one of skill in the art can adjust the figures for the non-self-hybridized embodiments as well). In such embodiments, rather than (or following) the amplification step depicted in FIG. 3 involving the amplification primer 60 (which can comprise, consist, or consist essentially of a universal region), one performs an amplification step to add a desired sequence (e.g., 71) to one end of the double-extended target primer via a different primer 70. This process, and the resulting product 702 are shown in FIG. 6 for a double-extended target primer that has a significant amount of target nucleic acid sequence in it, and in FIG. 7 (802), for a double-extended target primer that has an insignificant amount of target nucleic acid sequence in it.

In some embodiments, there is a first amplification primer 70 which, while including the universal region 20 (and optionally the noncomplementary region), includes an additional section 71. This section 71 allows one to customize the end(s) of the double-extended target primer. As will be appreciated by one of skill in the art, section 71 is not a "non-complementary" region, as defined herein, rather, it is a sequence that is not complementary to the sequence that the amplification primer 70 is hybridized to. The ability to have different sequences on each end of the nucleic acid segment can be useful in some sequencing applications. Thus, the above amplification primer 70 can be used in these situations. The primer 70 can include the noncomplementary region 30 and the universal region 20. As will be appreciated by one of skill in the art, different primers 70, each having a different section 71, can be added to specific double extended linear primers, allowing various double extended linear primers to be combined. In some embodiments, more than one amplification primer is used (e.g., two or more different sequenced primers, as depicted in FIG. 6 and processed in parallel, while still being able to identify the specific double extended linear primer). Of course, this can be adjusted for loopable primers as well.

As shown in the lower section of FIG. 6, when the target nucleic acid sequence 1 is included, amplification proceeds from these two primers to produce a double-extended target primers 702 (which need not be self-hybridized).

In contrast, as shown in FIG. 7, in those situations in which very little or no target nucleic acid sequence is included between the universal region 20 and its complement 20', the resulting structure has a relatively smaller insert section resulting in relatively less amplification through the use of the insert amplification primers (802) and/or the optional amplification step depicted in FIG. 3 (as noted above, this can be due to the faster hybridization kinetics due to the shorter linker and/or due to the smaller size of the loop structure which can physically limit processing of this area.

RNA Amplification

As noted above, various embodiments disclosed herein can be useful for the amplification of RNA sequences, such as mRNA. In some embodiments, the amplification embodiments disclosed herein can be selective for amplifying mRNA sequences over other types of RNA, and/or amplifying relatively longer pieces of RNA over shorter pieces of RNA. In some embodiments, the amplification of RNA sequences employs one or more of the target primers provided herein.

Figure 8:
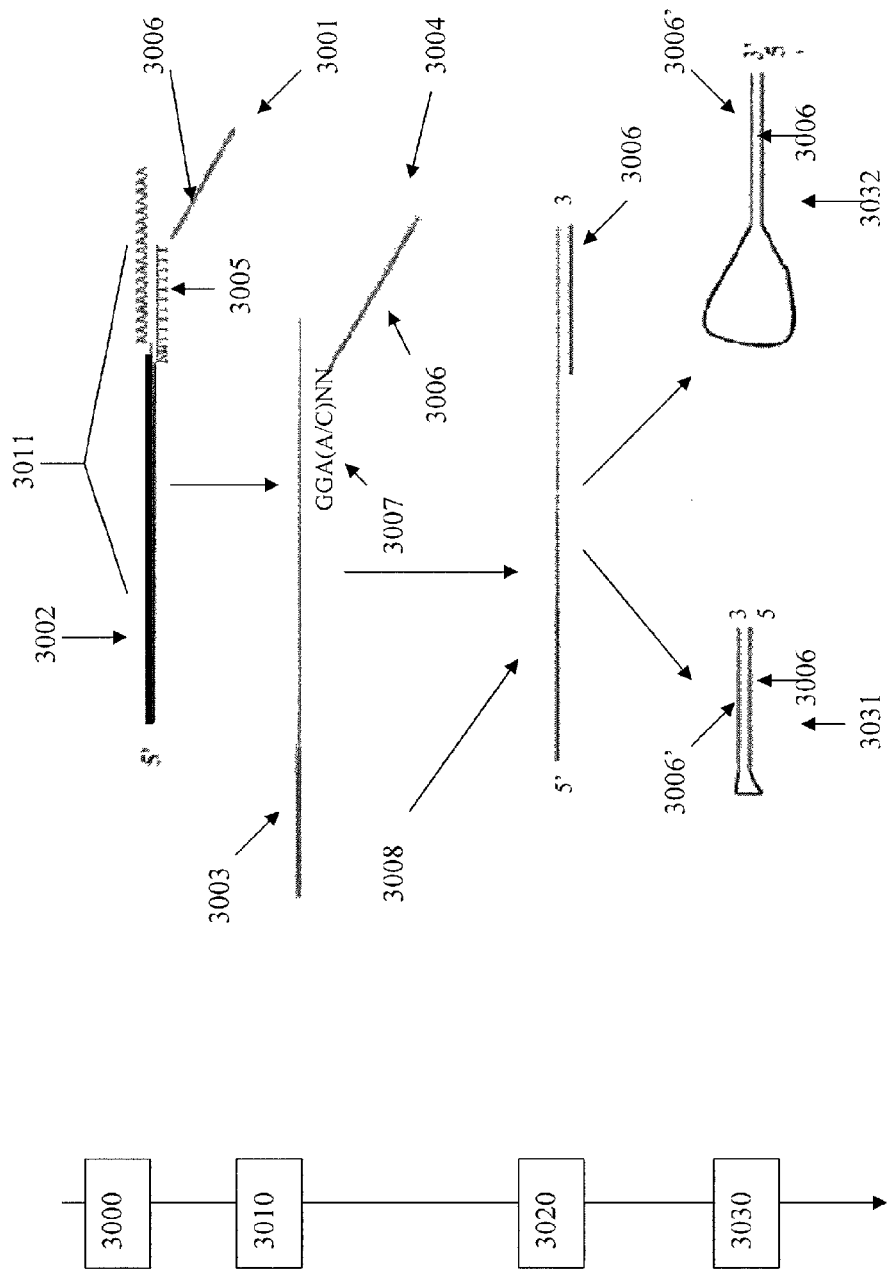
FIG. 8 depicts an embodiment of an amplification embodiment.

Some embodiments of the methods are outlined in FIG. 8. As shown in FIG. 8, the method can involve allowing a first target primer 3001 to hybridize to a target RNA sequence 3002 in process 3000. The first target primer 3001 can comprise a first universal region 3006 on its 5' end and a 3' target specific region 3005 that includes at least 6 thymines if not more (for example, 7, 8, 9, 10 or more thymines). These thymines can be useful in helping to selectively amplify mRNA sequences over other sequences that can be present in the starting sample.

In the depicted embodiment, the 3' target specific region 3005 comprises both a known region (a poly-thymine region) and a degenerate region ("V" "VN" or "NN", where V is A, C, or G). The degenerate region is optional. However, as will be appreciated by one of skill in the art, in light of the present disclosure, the presence of non-thymine residues allows for even greater selectivity for sequences that immediately abut a polyA region. Thus, the presence of one or more non-thymine residues can reduce internal polyA priming. In some embodiments, while it is known that there are at least 4 thymines present in the 3' target specific region, it need not be known if there are more than 4 thymines in the 3' target specific region.

Once the target primer 3001 is hybridized, it can be extended via a reverse transcription reaction to make an extended target primer 3003.

Following this extension, the extended target primer 3003 can be hybridized by a second target primer 3004 in process 3010. The second target primer 3004 can include the same universal region 3006 and a different 3' target specific region.

In the depicted embodiment, the 3' target specific region comprises a sequence that is, or is complementary to, a splice junction 3007. Thus, in some embodiments this further allows one to selectively amplify RNA sequences as opposed to non RNA sequences. The second target primer 3004 can then be extended to form a double extended target primer 3008. In some embodiments, the extended target primer 3003 includes an insert section 3011. As noted herein, the size of this insert section 3011 can vary depending upon the amount of the target nucleic acid sequence that is included between the two target primers. In some embodiments, the use of the splice junction further allows one to selectively manipulate mRNA over other forms of RNA.

Following this, the double extended target primer 3008 can, optionally, be amplified via an amplification primer that includes the universal region 3006, as shown in process 3020. During this process, and throughout any later amplification processes, the double extended target primers with very short or no foreign inserts, will rapidly form loops via the universal region 3006 and the universal region complement 3006', shown as structure 3031, and as denoted by process 3030. Such structures, 3031, will be effectively removed from further amplification processes (including both the optional amplification process 3020, as well as any insert primer amplification steps that may occur later). In contrast, those sequences that have a larger insert, will form the self-hybridized structure 3032 at a slower rate, thereby providing sufficient time for amplification primers (or insert amplification primers) to bind and amplify the double extended target primer. As noted elsewhere herein, in some embodiments, the insert section is large enough to allow for internal priming, even when the double extended target primer is self-hybridized 3032.

In some embodiments, a subsequent PCR or amplification reaction is performed which includes the use of insert primers or insert amplification primers. One or more such primers can be used to prime the insert section of the double extended target primer. The insert section can then be amplified. Of course, as noted above, sections with very small insert sections (such as primer dimers) will rapidly self-hybridize and be removed from the reaction. In contrast, double extended target primers with larger inserts will be relatively available for amplification via one or more insert amplification primers.

In some embodiments, any one of the above process can be repeated one or more times. In some embodiments, the above processes can occur concurrently, simultaneously, and/or sequentially.

Figure 9:
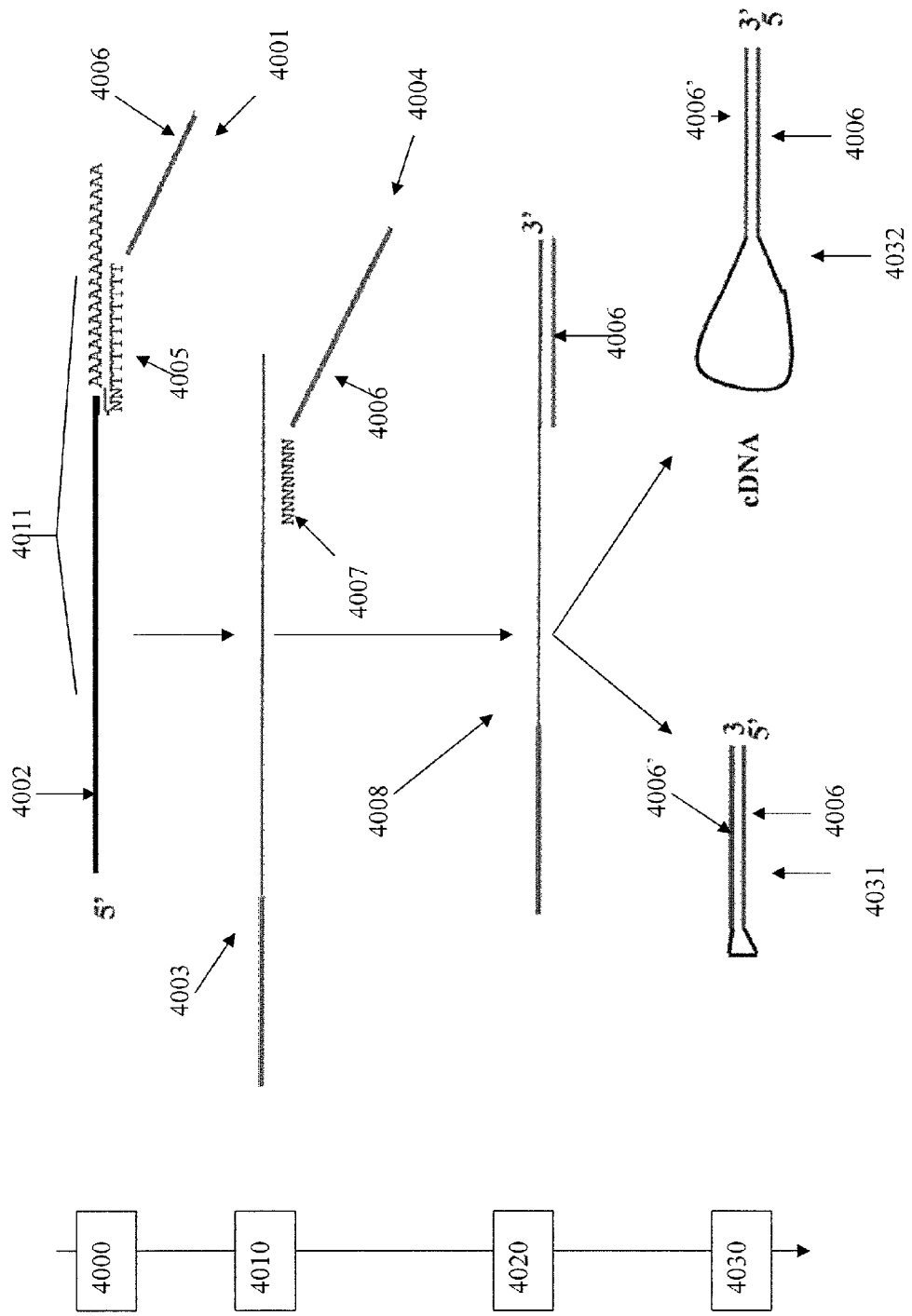
FIG. 9 depicts an embodiment of an amplification embodiment.

An additional set of embodiments is depicted in FIG. 9. While similar to the embodiments in FIG. 8, the second target primer does not have to be a 3' target specific region that specifically hybridizes to a splice site sequence. Rather, the second 3' target specific region in the second target primer comprises, consists, or consists essentially of a degenerate and/or random region. This allows for greater breadth of amplification following the formation of the extended target primer.

As shown in FIG. 9, in some embodiments, the method can include allowing a first target primer 4001 to hybridize to a target RNA sequence 4002 in process 4000. The first target primer 4001 can comprise a first universal region 4006 on its 5' end and a 3' target specific region 4005 that includes at least 6 thymines, if not more (e.g., 7, 8, 9, 10, 10-15, 15-20, etc.). As noted above, these thymines can be useful in helping to select the RNA sequences over other sequences that can be present in the starting sample. In the depicted embodiment, the 3' target specific region 4005 comprises both a known region (a poly T region) and a degenerate region ("V", "VN" or "NN"). The degenerate region is optional. In some embodiments, while it is known that the known region includes at least 4 thymines, it is not known how many thymines the known region includes.

Once the target primer 4001 is hybridized, it can be extended via a reverse transcription reaction to make an extended target primer 4003.

Following this extension, the extended target primer 4003 can be hybridized to a second target primer 4004 in process 4010. The second target primer 4004 can include the same universal region 4006 and a different 3' target specific region. In the depicted embodiment, the 3' target specific region 4007 comprises a sequence that is degenerate and will hybridize to the nucleic acid sequence in the extended target primer 4003. The second target primer 4004 can then be extended to form a double extended target primer 4008. In some embodiments, the extended target primer 4003 will include an insert section 4011. As noted herein, the size of this insert section 4011 can vary depending upon the amount of the target nucleic acid sequence that is included between the two target primers.

Following this, the double extended target primer 4008 can, optionally, be amplified via an amplification primer that includes the universal region 4006, as shown in process 4020. During this process, and throughout any later amplification processes, the double extended target primers with very short or no foreign inserts, will rapidly form loops via the universal region 4006 and the universal region complement 4006', shown as structure 4031, and as denoted by process 4030. Such structures, 4031, will be effectively removed from further amplification processes. In contrast, those sequences that have a larger insert, will form the self-hybridized structure 3032 at a slower rate, thereby providing sufficient time for amplification primers (or insert amplification primers) to bind and amplify the double extended target primer.

Figure 10A:
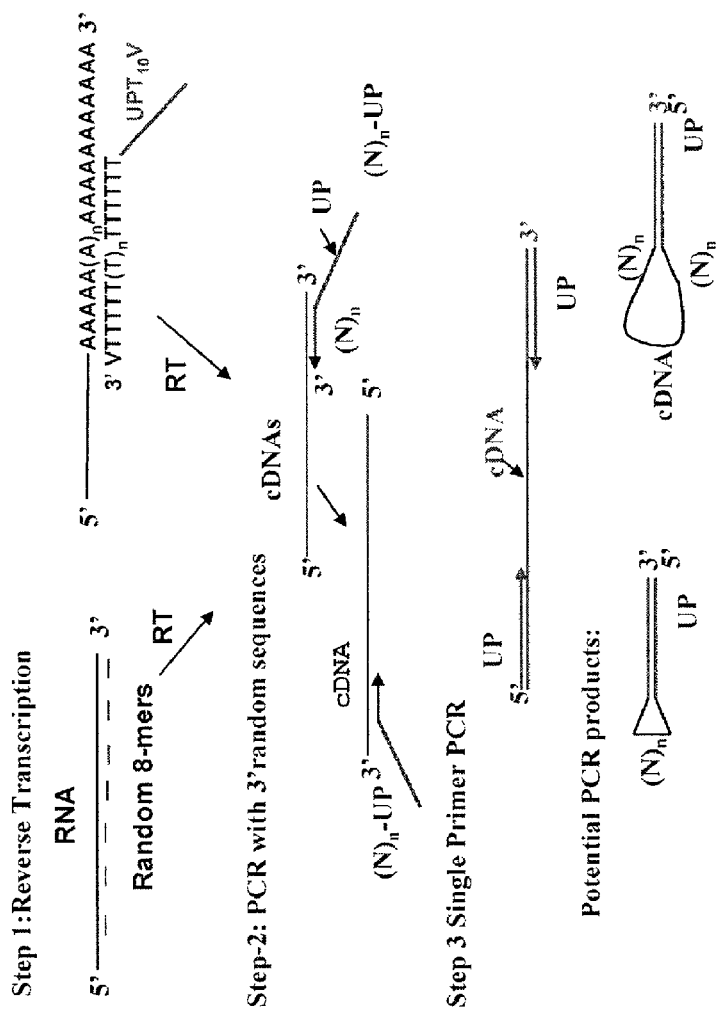
FIG. 10A depicts a general outline of some embodiments of a WTA with either a random primer RT or a polyT target primer RT.

In some situations, the embodiment in FIG. 9 is modified in the manner described in Example 4 and FIG. 10A. For example, in some embodiments, while the reverse transcription in process 4000 can occur to extend the target primer to form the extended target primer, the use of degenerate or random 3' specific regions in subsequent processes can either 1) result in a double extended primer where one end is the complement of the target primer 4001 and the other end is target primer 4004, as shown in FIG. 9, or 2) result in a double extended primer where one end is the complement of a degenerate target primer 4004, and the other end is a degenerate target primer 4004. This process is generally shown on the right-hand side of FIG. 10A. Thus, in some embodiments, the self-hybridizing regions are created from the primer involved in the reverse transcription and then the primer involved in the second strand synthesis. In some embodiments, the self-hybridizing regions are both added during the "second strand synthesis," second process 4010, or after the reverse transcription reaction has been performed. Of course, mixtures of both processes can occur during a single reaction. In some embodiments, more than two target primers can be used. For example, FIG. 10A depicts three different times when a target primer is used, none of which needs to use the same target primer (although they can have the same universal region). In some embodiments, the first process involves using a simple random primer to drive the reverse transcription reaction and then to use a first and second target primer on the resulting cDNA product from the reverse transcription reaction. An example of this is depicted on the left-hand side of FIG. 10A. Thus, in some embodiments, the reverse transcription reaction does not involve a target primer and the self-hybridizing regions are added after the reverse transcription reaction. The sequences in FIG. 10A include polyA and polyT sections.

The specific number of nucleotides in each section can vary, as denoted by the "n" subscript in the sequences. The "V" denotes A, C, or G. In some embodiments "n" is 0-100, for example 1-30, 1-20, 1-10, or 1-5.

The following discussion discloses additional alternative variations on the general embodiments disclosed above.

In some embodiments, each of the processes or steps denoted in FIG. 8 and/or 9 occur in the order denoted in the figure. In some embodiments, at least one of the processes overlaps with at least one process before or after the process. In some embodiments, one or more of the processes overlaps with another process. In some embodiments, one, two, three, or four of the noted processes can occur concurrently in a reaction volume or sample. In some embodiments, a first process is allowed to occur (by the addition of a first target primer and the extension thereof), and then a second process is commenced (e.g., by the addition of a second target primer). In some embodiments, a third process is commenced by the addition of an amplification primer and the amplification of the double extended target primer. In some embodiments, a fourth process is commenced by the addition of at least one insert amplification primer and the amplification of the insert section.

In some embodiments, one or more of the processes outlined in FIGS. 8 and/or 9 and the discussion relating thereto can be repeated one or more times. In some embodiments, one or more of processes 3000, 4000, 3010, 4010, 3020, 4020, 3030, and/or 4030 can be repeated at least once, for example, at least one of the following repetitions: 1, 5, 10, 20, 30, 40, 50, 100, 1000, 5000, or more times.

In some embodiments, the 3' target specific region that includes a splice site (e.g., 3007) can also include additional nucleotides. In some embodiments, any of the embodiments described herein involving a 3' target specific region that includes a splice site can be employed using a different splice site or a different known sequence. In some embodiments, the splice site that is used can comprise, consist, or consist essentially of the following: 5' AAGG3', 5'CAGG3'. In some embodiments, the 3' target specific region can further include one or more additional nucleotides. In some embodiments, the one or more additional nucleotides can be degenerate (e.g., a number of alternative sequences having various nucleotides at the degenerate positions). In some embodiments, the 3' target specific sequence comprises at least 1 additional nucleotide, for example, the 3' target specific sequence can comprise the above splice site and an additional 1, 2, 3, 4, 5, 6, 7, 8, 9, 10, 11, 12, or more nucleotides. In some embodiments, these additional nucleotides are known and/or degenerate.

In some embodiments, the target sequences to be examined comprise RNA. In some embodiments, the target sequences to be examined comprise mRNA. In some embodiments, mRNA in a sample is selectively amplified over other nucleic acids in the sample. In some embodiments, mRNA in a sample is selectively amplified over other RNAs in the sample. In some embodiments, the method allows for the selective amplification of mRNA over tRNA and/or ribosomal RNA. In some embodiments, the double extended target primer is created from DNA, such as cDNA. In some embodiments, the extended target primer is created from DNA, such as cDNA. In some embodiments, the extended target primer is created from mRNA.

In some embodiments, the method employs a poly-thymine 3' target specific region in the first or second target primer. In some embodiments, such a 3' target specific region can also include one or more degenerate, known, or random nucleotides, for example, 1, 2, 3, 4, 5, 6, 7, 8, 9, 10, 11, 12, or more degenerate, known, or random nucleotides. In some embodiments, the poly-thymine 3' target specific region comprises more than 1 thymine, for example, 2, 3, 4, 5, 6, 7, 8, 9, 10, 11, 12, or more thymines.

In some embodiments, the product that is created from the method comprises DNA, such as cDNA. In some embodiments, the method is applied via two rounds of reverse transcription, rather than just one, and is followed by in vitro transcription linear amplification from a promoter that is introduced in the first reverse transcription step. In both of the reverse transcription steps, a target primer is employed such that a double extended target primer is created.

In some embodiments, the method employs only a single round of reverse transcription. In some embodiments, the method does not include in vitro transcription. In some embodiments, the method avoids having to perform two rounds of reverse transcription and in vitro transcription, while still producing enough product for sequencing and/or detection.

As noted above, in some embodiments, the 3' target specific regions in the first and/or second target primer can comprise, consist, or consist essentially of degenerate nucleotides, known nucleotides, random nucleotides, more than one adenine, more than one thymine, RNA splice sites, and/or any combination thereof. In some embodiments, there is a third or subsequent target primer that can comprise, consist, or consist essentially of degenerate nucleotides, known nucleotides, random nucleotides, more than one adenine, more than one thymine, RNA splice sites, and/or any combination thereof.

In some embodiments, employing one or more of the herein disclosed target primers can allow for one to generally filter out non-RNA sequences from other nucleotides in a starting sample. In some embodiments, employing one or more of the target primers can also filter out non-mRNA sequences (such as tRNA or ribosomal RNA) from mRNA sequences. In some embodiments, employing one or more of the target primers disclosed herein can allow for meaningful transcriptome wide mRNA amplification from relatively small sample sizes. In some embodiments, the sample size can be an amount of total RNA from less than 10,000 cells, for example less than any of the following cell numbers: 1,000, 100, 10, or 1 cell. In some embodiments, the sample size can be an amount of mRNA from less than 10,000 cells, for example less than any of the following cell numbers: 1,000, 100, 10, or 1 cell. In some embodiments, the libraries that result from mRNA amplification using one or more of the herein disclosed target primers can be more meaningful as they have avoided amplifying a substantial portion of non-mRNA sequences during the amplification.

In some embodiments, amplification (via the amplification primer) can be achieved via single primer amplification. In other embodiments, the amplification can be achieved via a two primer amplification, by extending the primers beyond the 3' end of the universal primer. In embodiments involving a splice site in the 3' target specific region, the two amplification primers can comprise 5'UPNN(A/C)AGG3' and 5'UPT$_n$3' (where n is any value, e.g., 6-15) respectively. In the two primer embodiments involving a degenerate 3' target specific region, the two amplification primers can comprise 5'UP3' and 5'UPT$_n$3' (where n is any value, e.g., 1-16) respectively. As above, any primer that can selectively hybridize to these sequences (or that can selectively hybridize to sequences hybridized by these sequences) can also be employed. Thus, in some embodiments, the amplification can be a two primer amplification. In some embodiments, the amplification is a single primer amplification.

As will be appreciated by one of skill in the art, as the resulting amplified insert sections will be longer and avoid primer dimer biases, the method can be especially useful in situations in which longer lengths of mRNAs are to be sequenced.

In some embodiments, the method employing a splice site in or as the 3' target specific region can be especially useful in developing a library of mRNAs based upon the splice site, manipulating various sequences containing the splice site, and/or amplifying mRNA. In some embodiments, one or more of the target primers is used for transcriptome amplification. In some embodiments, the use of one or more of the target primers to create a double extended target primer allows for an amplification step that selects against small amplicons (e.g., primer dimers).

In some embodiments, the product (or the above method itself) can occur as part of, or for use in, a SOLiD™ sequencing process. In some embodiments, the technique can be employed for the sequencing of a transcriptome from very small RNA samples. In some embodiments, the total amount of RNA is 4 pg or more.

In some embodiments, any of the above methods can further include the addition of a relatively long, relatively high temperature incubation. The incubation can be long enough and at a great enough temperature so as to disrupt DNA/RNA hybrid formation. This step can occur at the end of the reverse transcription step when there is a DNA/RNA hybrid. In some embodiments, the high temperature incubation lasts for at least 5 minutes and is at least at 90 degrees C., for example, the temperature can be at 95° C. for a time of at least 10 minutes. This incubation can greatly increase the yield of the method.

In some embodiments, the methods disclosed herein allow one to avoid significantly amplifying or detecting rRNA in a sample, without having to actually remove the rRNA from the sample. Thus, in some embodiments, a kit is provided that includes one or more ingredients for the method described herein, while lacking ingredients required for removing rRNA from a sample. The kit can further include ingredients for sequencing the resulting amplified target nucleic acid sequence. In some embodiments, a kit is provided that includes a target primer that does not include a dT specific region. Thus, in some embodiments, while one of the target primers can include a dT specific region, at least one of the target primers will not include a dT specific region.

Additional Embodiments

As noted herein, the insert amplification can be done without actually forming a self-hybridized structure for the longer double extended target primers. In some embodiments, only the double-extended target primers that are primer dimers are self-hybridized during the insert amplification process. In some embodiments, at least the double-extended target primers that are primer dimers are self-hybridized during the insert amplification process. In some embodiments, the double-extended target primers that are self-hybridized during the insert amplification process comprise an insert section less than 200 nucleotides in length. In some embodiments, the double-extended target primers that are self-hybridized during the insert amplification process comprise an insert section less than 100 nucleotides in length. In some embodiments, at least the double-extended target primers that comprise an insert section less than 100 nucleotides in length are self-hybridized during the insert amplification process. In some embodiments, at least the double-extended target primers that comprise an insert section less than 200 nucleotides in length are self-hybridized during the insert amplification process.

In some embodiments, the process can produce whole transcriptome amplification DNA that can be readily reamplified via standard PCR. In some embodiments, the DNA is cDNA from mRNA.

In some embodiments, the 3' target specific region is the same for each 3' target specific region in the target primer. In some embodiments, the 3' target specific region is different for different target primers. In some embodiments, the 3' target specific region can comprise a degenerate sequence or random region, and thus, the primer comprises numerous different primers, at least some of which have different sequences at the 3' target specific region.

In some embodiments, the target nucleic acid sequence is from a single cell. In some embodiments, the target primer is a linear primer when it hybridizes to the target nucleic acid sequence. In some embodiments, the first target primer is a looped primer when it hybridizes to the target nucleic acid sequence.

In some embodiments, only a single universal region primer sequence is used in the PCR amplification (and/or pre-PCR) of any given PCR (and/or pre-PCR) amplified nucleic acid sequence. In some embodiments, in the PCR (and/or pre-PCR) amplification, only a single PCR (and/or pre-PCR) primer is used to amplify all of the PCR (and/or pre-PCR) amplified nucleic acid sequences. In some embodiments, in the PCR (and/or pre-PCR) amplification, only a single universal region nucleic acid sequence is used as a primer to amplify all of the PCR (and/or pre-PCR) amplified nucleic acid sequences.

In some embodiments, the temperature of the solution containing the double extended target primers is cooled, thereby allowing at least the shorter of the double-extended target primers to self-hybridize via the universal region and the sequence that is complementary to the universal region.

In some embodiments, the kit comprises reagents for a reverse transcription reaction. In some embodiments, the kit comprises one or more first target primers, which can include a universal region and a 3' target specific region. The 3' target specific region can include a poly-thymine region. In some embodiments, the 3' target specific region can also include one or more degenerate nucleotides. The kit can further include an amplification primer that is the same as at least part of the 5' universal region. In some embodiments, the kit further comprises one or more second target primers. In some embodiments, the second target primers can comprise the same 5' universal region as is present in the first primer and a 3' target specific region that corresponds to a RNA splice site sequence. In some embodiments, the second target primer can comprise the 5' universal region and a 3' target specific region that can comprise a degenerate sequence. In some embodiments, the kit comprises PCR reagents. In some embodiments, the kit can further include insert amplification primers to allow for the amplification of one or more of the insert sections. In some embodiments, these insert amplification primers are specific primers for specific sequences. In some embodiments, the insert amplification primers are specific for mRNA sequences or sequences that are adjacent to such mRNA sequences. As will be appreciated by one of skill in the art, one or more of the same and/or different first and/or second primers can be included in the kits. Of course, when a degenerate primer is present, more than one primer will necessarily be present. In some embodiments, the kits can serve to expedite the performance of the methods of interest by assembling two or more components used in carrying out the methods. In some embodiments, kits can contain components in pre-measured unit amounts to minimize the need for measurements by end-users. In some embodiments, kits can include instructions for performing one or more methods of the present teachings. In certain embodiments, the kit components are optimized to operate in conjunction with one another.

In some embodiments, the present teachings provide a method of using target primers to amplify an entire population of mRNAs from a single small sample on the order of one or a few cells from an eukaryote. In some embodiments, the amplified mRNA products produced by this strategy can be readily assayed by micro-array platforms, such as AB1700, and/or real time PCR platforms commercially available from Applied Biosystems.

In some embodiments, the use of a target primer as described above allows one to analyze especially low amounts of target nucleic acid in whole transcriptome amplification. For example, in some embodiments, the initial sample contains less than 1 gram of target nucleic acid sequence, for example, 1000-100, 100-10, 10-1, 1-0.1, 0.1-0.01, 0.01-0.001, 0.001-0.0001, 0.0001-0.00001, 0.00001-0.000001 nanograms or less. In some embodiments, the amount of target nucleic acid is the amount of the target nucleic acid in a single cell. In some embodiments, the amount of target nucleic acid is between 0.5 and 100 pg. In some embodiments, the amount of target nucleic acid is less than 100 pg. As will be appreciated by one of skill in the art, this can be especially advantageous in whole transcriptome amplification and sequencing.

In some embodiments, any of the methods can be applied in or for a clinical and/or forensics environment. In some embodiments, the technique is applied in molecular oncology. In some embodiments, the technique is applied to a sample that comprises at least one cell, for example 1, 1-10, 10-100, 100-1000, or more cells. As will be appreciated by one of skill in the art, this can be especially advantageous for whole transcriptome amplification and sequencing. In some embodiments, this can be used in laser captured single cells.

In some embodiments, the relatively large increases in amplification are achieved while still maintaining a significant amount of dose response during the amplification. For example, in some embodiments, relatively small amounts of one species to be amplified will still be a relatively small percent of the amplified product (although it could have been amplified, e.g., 100-1,000,000 times). As will be appreciated by one of skill in the art, this can be especially advantageous in whole transcriptome amplification and sequencing.

As will be appreciated by one of skill in the art, while single primer amplification embodiments ameliorates the problem of random background sequence amplification, it can introduce kinetic parameters that impact the levels of amplification. During the formation of the double extended target primer, with every thermal cycle a significant amount of primer can be removed by primer-primer hybridization and extension. As such, in some embodiments, it can be advantageous to use relatively high levels of primer. In some embodiments, 10 micromolar or more can be used, for example, 10-100, 100-1000, 1000-10,000, 10,000-100,000 micromolar can be used. In some embodiments new primer can be added during or throughout the procedure.

In some embodiments, the target primer (and its methods of use) allows one to use a 3' target specific region that is not constrained to just A or G in whole transcriptome amplification. In some embodiments, the 3' target specific region is or includes a random and/or degenerate region. In some embodiments, this region includes T and/or C in the random region. As will be appreciated by one of skill in the art, this does not mean that the region is no longer "random." In some embodiments, the random region can include at least three different nucleotides (e.g., A, G and T or C; or T, C, and A or G). In some embodiments the random region can include at least four different nucleotides.

In some embodiments, the random region includes at least one thymine. In some embodiments, the random region includes at least one cytosine. In some embodiments, at least one of the primers in the amplification reaction includes a cytosine and/or thymine in the random region. In some embodiments, at least one of the primers in the amplification reaction includes, in the random region, at least one nucleotide that is not an adenine or a guanine. In some embodiments, the base or nucleotide is or comprises a thymine, cytosine, or uracil, nucleotide analog (e.g., including thymine, uracil, and/or cytosine analogs), or other option. In some embodiments, the random region includes at least 2, 3, 4, 5, 6, 7, 8, 9, 10, 11, 12, or more nucleotides that are cytosine and/or thymine. In some embodiments, the random region includes at least 2, 3, 4, 5, 6, 7, 8, 9, 10, 11, 12, or more nucleotides that are not adenine and/or guanine. As will be appreciated by one of skill in the art, removing this constraint can be especially advantageous in WTA applications and sequencing.

In some embodiments, the use of a target primer allows one to analyze samples that are relatively large in volume compared to standard whole transcriptome amplification techniques. For example, in some embodiments, the sample is more than 60 nl, for example, 60-80, 80-100, 100-200, 200-500, 500-600, 600-601, 601, 500-1000, 1000-10,000, 10,000-100,000, 100,000-1,000,000 nl or more in volume. In some embodiments, an initial sample is diluted or brought up to a volume that is above 60 nl, for example, 60-80, 80-100, 100-200, 200-500, 500-1000, 1000-10,000, 10,000-100,000, 100,000-1,000,000 nl or more. In some embodiments, a sample to be analyzed starts off as a dry or non-liquid sample and a volume of liquid is added to the sample to suspend the sample. In some embodiments, the volume used to suspend the sample is more than 60 nl, for example, 60-80, 80-100, 100-200, 200-500, 500-1000, 1000-10,000, 10,000-100,000, 100,000-1,000,000 nl or more. In some embodiments, any one or more of the processes outlined in FIG. 9 is carried out in a volume that is above 60 nl, for example, 60-80, 80-100, 100-200, 200-500, 500-600, 601, 600-1000, 1000-10,000, 10,000-100,000, 100,000-1,000,000 nl or more. In some embodiments, at least one of the amplification processes in FIG. 9 is carried out in a volume that is above 60 nl, for example, 60-80, 80-100, 100-200, 200-500, 600, 601, 500-1000, 1000-10,000, 10,000-100,000, 100,000-1,000,000 nl or more. As will be appreciated by one of skill in the art, removing the volume constraint can be especially advantageous in WTA applications and sequencing.

As will be appreciated by one of skill in the art, the above embodiments can be achieved via the use of a target primer that results in the formation of a double extended target primer that can self-hybridize (at least for the shorter double-extended target primers). Thus, in some embodiments, eventually the amplified DNA will have two sections that can self-hybridize. In some embodiments, this is achieved via the use of a single target primer in the amplification reaction (such that the amplified DNA has a sequence that is the target primer on one end and the complement of the target primer on the opposite end). In some embodiments, this can be achieved via the use of different primers, where all of the primers share a common sequence (such as the universal region, a random region, and/or a noncomplementary region) such that they can still produce the double extended target primer that can self-hybridize.

Additional Embodiments

In some embodiments, the use of a target primer as described above allows one to analyze especially low amounts of target nucleic acid in whole transcriptome amplification. For example, in some embodiments, the initial sample contains less than 1 gram of target nucleic acid sequence, for example, 1000-100, 100-10, 10-1, 1-0.1, 0.1-0.01, 0.01-0.001, 0.001-0.0001 nanograms or less. In some embodiments, the amount of target nucleic acid is the amount of the target nucleic acid in a single cell. In some embodiments, the amount of target nucleic acid is between 0.5 and 100 pg. In some embodiments, the amount of target nucleic acid is less than 100 pg. As will be appreciated by one of skill in the art, this can be especially advantageous in whole transcriptome amplification and sequencing.

In some embodiments, because the target primers are not biased in how they initially bind to the target nucleic acid sequence (e.g., in contrast to looped primers), they can bind along and within stretches of DNA or RNA, thereby avoiding having to over process the target to make relatively short pieces of DNA or RNA for amplification. In some embodiments, the method avoids or does not require overprocessing the initial sample.

In some embodiments, by using the herein presented techniques, one can avoid a precleaning step, such as fragment size selection. Thus, in some embodiments, the method does not include a precleaning step, such as fragment size selection.

In some embodiments, any of the methods can be applied in or for a clinical and/or forensics environment. In some embodiments, the technique is applied in molecular oncology.

In some embodiments, the relatively large increases in amplification are achieved while still maintaining a significant amount of dose response during the amplification. For example, in some embodiments, relatively small amounts of one species to be amplified will still be a relatively small percent of the amplified product (although it could have been amplified, e.g., 100-1,000,000 times).

As will be appreciated by one of skill in the art, while a single primer amplification embodiment ameliorates the problem of random background sequence amplification, it can introduce kinetic parameters that impact the levels of amplification (during the second strand synthesis, e.g., 3010 or 4010). During the formation of the double extended target primer, with every thermal cycle a significant amount of primer is expected to be removed by primer-primer hybridization and extension. As such, in some embodiments, it can be advantageous to use relatively high levels of primer.

In some embodiments, the target primer comprises, consists, or consists essentially of relatively short 3' target specific regions, such as a short 3' random region. In some embodiments, this shorter 3' target specific region is used in whole transcriptome amplification where one starts with a low amount of RNA. In some embodiments, the 3' target specific region is less than 12 nucleotides in length, for example, 11, 10, 9, 8, 7, 6, 5, 4, or 3 nucleotides. In some embodiments, the 3' target specific region is between 9 and 2, 8 and 3, 7 and 3, 6 and 3, or 6 and 4 nucleotides in length.

In some situations, after incorporation of a universal region and during the second strand synthesis (e.g., 3010 and 4010), universal primers will still have a problem of having some homology with internal sequences in highly complex populations of long fragments. Where the concentration of the universal primers are typically on a μM scale, even partial matches of the 3' end of the universal primers with internal sequences of DNA fragments can generate shorter products. These shorter products can be preferentially amplified by high concentrations of universal primers. Thus, some of the present embodiments can be used to limit the generation of these short products from primer-dimers or spurious internal priming.

In some embodiments long tracts of dT bases can be used in the target primer (as a noncomplementary region for example) for the above reason. In other embodiments, tracts of sequences rarely found in the target transcriptome are used as a noncomplementary region. Any sequence that reduces the likelihood that primer dimers will form can be employed As will be appreciate by one of skill in the art, while the 3' target specific region often includes a random or degenerate region, in some embodiments, the sequence is a specific sequence or collection of specific sequences. In some embodiments, the target primer can include additional sequence sections to those described above. In other embodiments, the target primer only includes those sections depicted in FIG. 1A and/or 1C. As will be appreciated by one of skill in the art, some of the presently disclosed techniques can be applied to RNA amplification as well, for example, by including an initial reverse transcription step.

As will be appreciated by one of skill in the art, in some embodiments, a noncomplementary region is used throughout numerous primers, allowing for multiple primers, such as primers including universal, random, or degenerate regions, to be used with a reduced risk of undesired priming events. This can be useful in multiplexed reactions in which numerous different starting primers are employed.

In some embodiments, the above methods can allow for a significant amount of amplification to occur. In some embodiments, the amplification is of nucleic acid sequences of a significant length (e.g., 200 or more nucleic acids). In some embodiments, the amplification of these lengths of target nucleic acid sequences is achieved. In some embodiments, at least a fraction of the transcriptome is amplified, e.g., 0-1, 1-5, 5-10, 10-20, 20-30, 30-40, 40-50, 50-60, 60-70, 70-80, 80-90, 90-95, 95-99, or 99-100% of the transcriptome is amplified. In some embodiments, at least some fraction of the fraction amplified is of the desired length, e.g., 0-1, 1-5, 5-10, 10-20, 20-30, 30-40, 40-50, 50-60, 60-70, 70-80, 80-90, 90-95, 95-99, or 99-100% is at least 200 by in length.

In some embodiments, the amount of amplification across a transcriptome is substantially similar. In some embodiments, the amount of amplification for the various target nucleic acids sequences is the same. In other words, sequences A-Z are all amplified to a similar extent so that the resulting ratio of product nucleic acid sequences is the substantially the same for sequences A-Z. In some embodiments, the ratios are maintained in a qualitative manner (e.g., there is more of sequence A than sequence B).

In some embodiments, the amount of amplification of the desired fragments that is achieved is substantial. For example, amplification of the initial product over 30 fold can be achieved, e.g., 30-100, 100-1000, 1,000-3000, 3000-10,000, 10,000-50,000, 50,000-100,000, 100,000-500,000, 500,000-800,000, 800,000-1,000,000, 1,000,000-10,000,000 fold or more. In some embodiments this is achieved with a reduced amount of primer dimer formation and/or spurious priming. In some embodiments, the amount of primer dimers is reduced by at least some amount, e.g., 0-1, 1-5, 5-10, 10-20, 20-30, 30-40, 40-50, 50-60, 60-70, 70-80, 80-90, 90-95, 95-99, or 99-100%.

As noted above, some of the embodiments can be advantageously used when random and/or degenerate priming regions are employed at the 3' target specific region of the primer, when universal primers are used, or when both aspects are used. Moreover, in some embodiments, further benefits can be obtained when numerous such primers (or other non-target primers) are combined within a reaction (such as in multiplexed or subsequent amplification or extension reactions). As such, as noted above, some of the embodiments can be useful for whole transcriptome amplification. However, not all of the disclosed embodiments are limited to such applications. Even amplification reactions that do not include random regions, or do not involve whole transcriptome amplification can benefit from some of the above embodiments. For example, some of the above embodiments will reduce the number or amount of relatively short nucleic acid sequences that are amplified from a target. As will be appreciated by one of skill in the art, these shorter sequences can be problematic for a variety of reasons (e.g., since they are shorter, they will dominate subsequent amplification reactions). Additionally, the insertion of the noncomplementary region generally allows for one to use either a random, specific, or mix thereof, region for target hybridization, while reducing the likelihood that the target sequence will hybridize too frequently or nonspecifically.

In some embodiments, the target primers and relevant methods are employed in massively multiplexed procedures in which various target primers are employed. As will be appreciated by one of skill in the art, the above embodiments employing degenerate ends at the 3' target specific region of the probe is one form of multiplexing. However, in some embodiments, different sequences are also employed within the target primer so as to provide a degree of separation or distinctness among the amplified products. In some embodiments, these different sequences are in the universal priming section, a tag sequence, or other additional section added to the target primer. In some embodiments, the number of primers having these different sequences (apart from differences in the 3' target specific region) are at least 2, if not more, for example, 2-5, 5-10, 10-20, 20-30, 30-50, 50-100, 100-200, or more primers can be used. In some embodiments, the primers can include specific bar-code sequences to allow for ease of identification.

Aspects of the present teachings may be further understood in light of the following examples, which should not be construed as limiting the scope of the present teachings in any way.

EXAMPLE 1

In some embodiments, one or more target RNA molecules can be amplified by employing one or more of the target primers described above. One can allow a first target primer to hybridize to mRNA. The first target primer can comprise a poly-thymine region and one or more degenerate nucleotides at the 3' end of the target primer. A reverse transcription reaction can then be performed using this first target primer to create an extended target primer.

Following or concurrently with the above step, a second target primer can be used to further amplify the extended target primer into a double extended target primer. This second target primer can include a splice site sequence (or a sequence that corresponds to a splice site sequence), and thereby hybridize to extended target primer at a sequence that would be a splice site. This second target primer can then be extended to create a double extended target primer.

Following or concurrently with this, the double extended target primer can optionally be amplified using an amplification primer. The amplification primer can have the same sequence as the universal region, or can be a subset of the universal region.

Following or concurrently with this, the insert section within the double extended target primer can be amplified using two insert amplification primers. While shorter double extended target primers can self-hybridize rapidly, and thereby remove themselves from the amplification, the longer double extended target primers will self-hybridize more slowly, and thus provide the insert amplification primers with adequate time, and/or space, to allow for amplification of the insert section.

EXAMPLE 2

In some embodiments, one or more target RNA molecules can be amplified by employing one or more of the target primers described above. One can allow a first target primer to hybridize to mRNA. The first target primer can comprise a poly-thymine section and one or more degenerate nucleotides at the 3' end of the target primer. A reverse transcription reaction can then be performed using this first target primer to create an extended target primer. Following this, a high temperature incubation can be performed. The high temperature incubation can be for 10 minutes at 95 degrees C.

Following or concurrently with the above step, a second target primer can be used to further amplify the extended target primer into a double extended target primer. This second target primer can include a degenerate sequence, including 6 or more degenerate oligonucleotides (and therefore include the corresponding number of primers). This second target primer can hybridize to the extended target primer. The second target primer can then be extended to create a double extended target primer.

Following or concurrently with this, the double extended target primer can optionally be amplified using an amplification primer. The amplification primer can have the same sequence as the universal region, or can be a subset of the universal region.

Following or concurrently with this, the insert section within the double extended target primer can be amplified using two insert amplification primers. While shorter double extended target primers can self-hybridize rapidly, and thereby remove themselves from the amplification, the longer double extended target primers will self-hybridize more slowly, and thus provide the insert amplification primers with adequate time, and/or space, to allow for amplification of the insert section.

EXAMPLE 3

Insert Amplification—Primer Pools

As will be appreciated by one of skill in the art, insert amplification can be achieved based on knowing which sequence was (or should be) contained within the insert, such as RNase P. In situations in which the target within the insert is not initially known, the protocol can be varied slightly to take this variable into account. For example, indiscriminant primers could be used. Alternatively, and as described in this example, numerous primers can be tested or used on the amplified sample.

Following any of the above initial amplification procedures (e.g., at a point following the formation of the double-extended target primer, but prior to the use of an insert amplification primer) one can divide the amplified product into numerous subsamples. Each subsample will simply be a fraction of the amplified product, and thus can include a representative (e.g., proportionate and substantially complete) distribution of the various double-extended target primers. Each subsample can be placed in a separate well, to which a specific known, or knowable, insert amplification primer, or primers, can be added. Following this, an amplification step can be performed in each of the wells. This will allow for the amplification of the insert section of the self-hybridized double-extended target primer. These amplified sequences can then be detected, such as by sequencing.

EXAMPLE 4

The following example compares the effectiveness of various embodiments of mRNA amplification using various target primers and other primers.

General Technique

The experiments in the present example involved a three process procedure to produce amplified cDNA. This example examines 1) the influence of the primer used in the first process (a reverse transcription process) and 2) the ability of the various embodiments to amplify mRNA in a mixture of total RNA and do so over a range of starting concentrations of mRNA.

To examine the first item above, two different approaches were used for the first process. The two approaches in the method are depicted in FIG. 10A.

For the first approach, the first process involved priming for a reverse transcription ("RT") reaction by using simple random primers (FIG. 10A, left-hand side). This set of experiments has been referred to as being the "random primer" RT approach.

For the second approach, the first process was a reverse transcription using a primer with a 3' poly(T) sequence that has a A,C or G on the 3' end and an universal primer (UP) on the 5' end (V-T10-UP (SEQ ID NO: 1), where, V represents A, C or G and UP is universal primer designed to contain 10 T's on its 3'end to augment the initial RT reaction and to reduce primer-primer interactions). This second approach has been referred to as being the "polyT target primer" approach.

As shown in FIG. 10A, following either the first or second approach, the remaining processes in the method were the same.

Specific Parameters

The RT reactions were done in 10 μL, containing: 2 μL RNA sample (4 pg-400 pg); 1 μL 10× cDNA Archiving kit buffer (Applied Biosystems); 2 μL of MMLV (50 U/μL); 0.5 μL 100 mM dNTPs; 1 μL 100 uM V-T10-UP (SEQ ID NO: 1) primer (or $UPN_{(n)}$; 0.3 μL 100 mM $MgCl_2$; 3.2 μL $H_2O$. The RT reaction mix was incubated at 42° C. for 30 minute and then 95° C. for 10 minute to inactivate MMLV as well as to dissociate and fragment RNAs.

The second process was the repeated hybridization and extension of random sequences to cDNAs produced in the first process. The target primers for this reaction had random sequences as their 3' specific regions, followed by 10 T's and then an arbitrary sequence on the 5' end [$UPdN_{(n)}$]. As noted in Example 5, the random region had 8 nucleotides.

The reaction for the second process was performed in 25 μL containing: 10 μL RT products; 2 μL 10× PCR Buffer II (Applied Biosystems); 1.25 μL 100 μM primer With random sequence on the 3' end (5' TCATGATCCGTGGAGTCG-GCTTTTTTTTTTN$_n$3'(SEQ ID NO: 2, $UPN_{(n)}$, where n=5-12 nucleotides); 5 μL AmpliTaq®, 5 U/μL; 1.25 μL 100 mM dNTPs; 0.75 μL 100 mM Mg $Cl_2$; 4.25 μL $H_2O$. The reaction mix was heated to 95° C. for 1 minute and then given 20 cycles of the following temperature pattern: 95° C. for 15 seconds, 16° C. for 2 minutes, 35° C. for 2 minutes, 65° C. for 2 minutes.

The third process was a single primer PCR at higher stringency. The primer in this case comprised the universal primer. The amplification of background contaminating sequences created by the hybridization and extension of random priming sequences in step 2 was curtailed in process 3 (and in process 2) because their self-hybridizing structures were too stable to permit efficient hybridization and extension during PCR. The hairpin structures had a calculated melting temperatures in excess of 80° C.

The reaction for process 3 was done in 40 μL containing: 25 μL of the products from step 2; 4 μL 10×PCR Buffer II (Applied Biosystems); 2 μL 100 μM UP primer (5'TCAT-GATCCGTGGAGTCGGCTTTTTTTTTT3'(SEQ ID NO: 3)); 4 μL AmpliTaq®, 5 U/μL; 1 μL 100 mM dNTPs; 0.6 μL 100 mM $MgCl_2$; 3.4 μL $H_2O$. The reaction mix of step 3 was Heated to 95° C. for 1 minute and then given 20 cycles of the following temperature pattern: 95° C. for 15 seconds, 65° C. for 2 minutes, 72° C. for 2 minutes. The 40 μL WTA products were combined with 4 mL 2× universal master mix (Applied Biosystems) and 2.36 mL $H_2O$. Then, 8 uL of sample mixture was pipetted into each of the wells on a 384 well plate that was preloaded with 2 μL of gene specific 900 nM forward/reverse primers, AmpliTaq Gold® polymerase and 250 nM TaqMan probe. TaqMan reactions were performed on AB7900 with the following profile: 95° C. for 10 min. to activate the Ampli-Taq Gold® polymerase, then 40 cycles of 95° C. for 15 sec and 60° C. for 1 min.

Amplification of Actb and 18S cDNA for Random Primer and PolyT Target Primer Reverse Transcription The above processes were performed for the amplification of Actb and 18S cDNA using the random primer and the polyT target primer for the reverse transcription process. The random primer length (and 3' target specific region) were 8 nucleotides in length.

Table 1 displays the results for the two different approaches. Table 1 contains the Ct values for mRNA of Actb (β-actin) and 18s rRNA with estimates of the relative amounts of amplification in the last two columns. Table 1A has Ct values for total RNAs from 40 ng to 4 pg using the random primer RT approach. Table 1B has Ct values for total RNAs from 40 ng to 4 pg using the polyT target primer approach. Table 1C has Ct values for purified mRNAs from 40 ng to 4 pg using the random primer RT approach. Table 1D has Ct values for purified mRNAs from 40 ng to 4 pg using the polyT target primer approach.

TABLES 1A-1D

'T20V' IS DISCLOSED AS SEQ ID NO: 4.

| A | random primer RT | Actb (RT only) | SD | 18S (RT only) | SD | Actb (WTA) | SD | 18S (WTA) | SD | Amplification folds for Actb | Amplification folds for 18S |
|---|---|---|---|---|---|---|---|---|---|---|---|
| total RNAs | 40 ng | 18.95 | 0.22 | 11.80 | 0.05 | 16.38 | 0.06 | 11.70 | 0.94 | 950 | 172 |
| total RNAs | 4 ng | 25.43 | 0.34 | 15.79 | 0.54 | 18.87 | 0.14 | 14.34 | 0.06 | 15118 | 439 |
| total RNAs | 400 pg | 27.01 | 0.04 | 19.76 | 0.33 | 24.47 | 0.32 | 19.78 | 0.17 | 935 | 158 |
| total RNAs | 40 pg | 31.06 | 0.34 | 24.55 | 0.14 | 40.00 | 0.00 | 23.03 | 0.37 | 0 | 462 |
| total RNAs | 4 pg | 34.23 | 0.55 | 27.35 | 0.22 | 40.00 | 0.00 | 24.50 | 0.58 | 3 | 1151 |
| total RNAs | NTC | 40.00 | 0.00 | 30.49 | 0.09 | 40.00 | 0.00 | 28.48 | 0.28 | | |

| B | T7-T20V RT | Actb (RT only) | SD | 18S (RT only) | SD | Actb (WTA) | SD | 18S (WTA) | SD | Amplification folds for Actb | Amplification folds for 18S |
|---|---|---|---|---|---|---|---|---|---|---|---|
| total RNAs | 40 ng | 19.01 | 0.05 | 20.66 | 0.03 | 13.04 | 0.35 | 19.94 | 0.42 | 10029 | 263 |
| total RNAs | 4 ng | 22.61 | 0.42 | 23.56 | 0.14 | 15.92 | 0.23 | 22.32 | 0.28 | 16603 | 380 |
| total RNAs | 400 pg | 26.69 | 0.00 | 25.77 | 0.25 | 17.42 | 0.79 | 19.17 | 0.04 | 98284 | 15543 |
| total RNAs | 40 pg | 29.57 | 0.28 | 27.76 | 0.18 | 26.50 | 0.86 | 29.25 | 0.10 | 1347 | 57 |
| total RNAs | 4 pg | 32.74 | 0.44 | 28.60 | 0.34 | 40.00 | 0.00 | 40.00 | 0.00 | 1 | 0 |
| total RNAs | NTC | 40.00 | 0.00 | 34.64 | 0.23 | 40.00 | 0.00 | 40.00 | 0.00 | | |

| C | random primer RT | Actb (RT only) | SD | 18S (RT only) | SD | Actb (WTA) | SD | 18S (WTA) | SD | Amplification folds for Actb | Amplification folds for 18S |
|---|---|---|---|---|---|---|---|---|---|---|---|
| mRNAs | 40 ng | 17.26 | 0.12 | 18.82 | 0.48 | 13.49 | 0.17 | 14.49 | 0.51 | 2183 | 3217 |
| mRNAs | 4 ng | 20.28 | 0.35 | 20.59 | 0.65 | 14.20 | 0.22 | 13.62 | 0.22 | 10801 | 19973 |
| mRNAs | 400 pg | 24.34 | 0.49 | 24.48 | 0.60 | 16.95 | 0.41 | 15.37 | 0.20 | 26773 | 88458 |
| mRNAs | 40 pg | 27.58 | 0.42 | 27.33 | 0.03 | 22.87 | 0.60 | 22.41 | 0.52 | 4200 | 4837 |
| mRNAs | 4 pg | 31.13 | 0.34 | 30.71 | 0.19 | 23.22 | 0.91 | 33.79 | 0.93 | 38493 | 19 |
| mRNAs | NTC | 40.00 | 0.00 | 35.33 | 0.02 | 40.00 | 0.00 | 40.00 | 0.00 | | |

| D | T7-T20V RT | Actb (RT only) | SD | 18S (RT only) | SD | Actb (WTA) | SD | 18S (WTA) | SD | Amplification folds for Actb | Amplification folds for 18S |
|---|---|---|---|---|---|---|---|---|---|---|---|
| mRNAs | 40 ng | 16.75 | 0.18 | 27.14 | 0.01 | 15.18 | 0.03 | 23.36 | 0.05 | 474 | 2203 |
| mRNAs | 4 ng | 20.08 | 0.18 | 27.30 | 0.24 | 14.58 | 0.05 | 21.93 | 0.22 | 7262 | 6609 |
| mRNAs | 400 pg | 23.61 | 0.07 | 30.23 | 0.09 | 15.96 | 0.31 | 24.23 | 0.59 | 32210 | 10254 |
| mRNAs | 40 pg | 26.90 | 0.12 | 33.23 | 0.12 | 17.09 | 0.17 | 24.65 | 1.20 | 144111 | 61036 |
| mRNAs | 4 pg | 29.78 | 0.02 | 33.47 | 0.11 | 23.83 | 0.33 | 26.44 | 0.75 | 9893 | 20910 |
| | NTC | 40.00 | 0.00 | 36.15 | 0.10 | 33.44 | 0.51 | 32.93 | 0.16 | | |

The amplification folds were calculated from the Ct values of the same sample from RT only and WTA reactions. For example, in Table 1D the amplification of Actb for 40 pg of mRNA was calculated in the following way: Ct(RT only) =26.90, Ct(WTA)=17.09, then, the amplification fold=$2^{(26.90-17.09)}\times$dilution factor (=160)=900×160=144,000 folds. 160 was the dilution factor.

Table 1A and 1B show that random primer RT approach fails to prime Actb mRNA at the single cell level of total RNA input while the polyT target primer approach primes down to the single cell level but fails at 4 pg levels of RNA, which represent about 1/10th of a cell's total amount of RNA. Table 1C, however, shows that random priming works for the Actb gene for RNA fractions enriched in mRNA by prior oligo dT binding purification (Poly(A)Purist™ mRNA Purification Kit) that can remove 99% of rRNA from total RNA. In Table 1C, 18S amplification in mRNA fractions is probably a reasonable indication of rRNA contamination because the reaction for 18S is no longer saturated as it is in Table 1A.

Figure 10B:
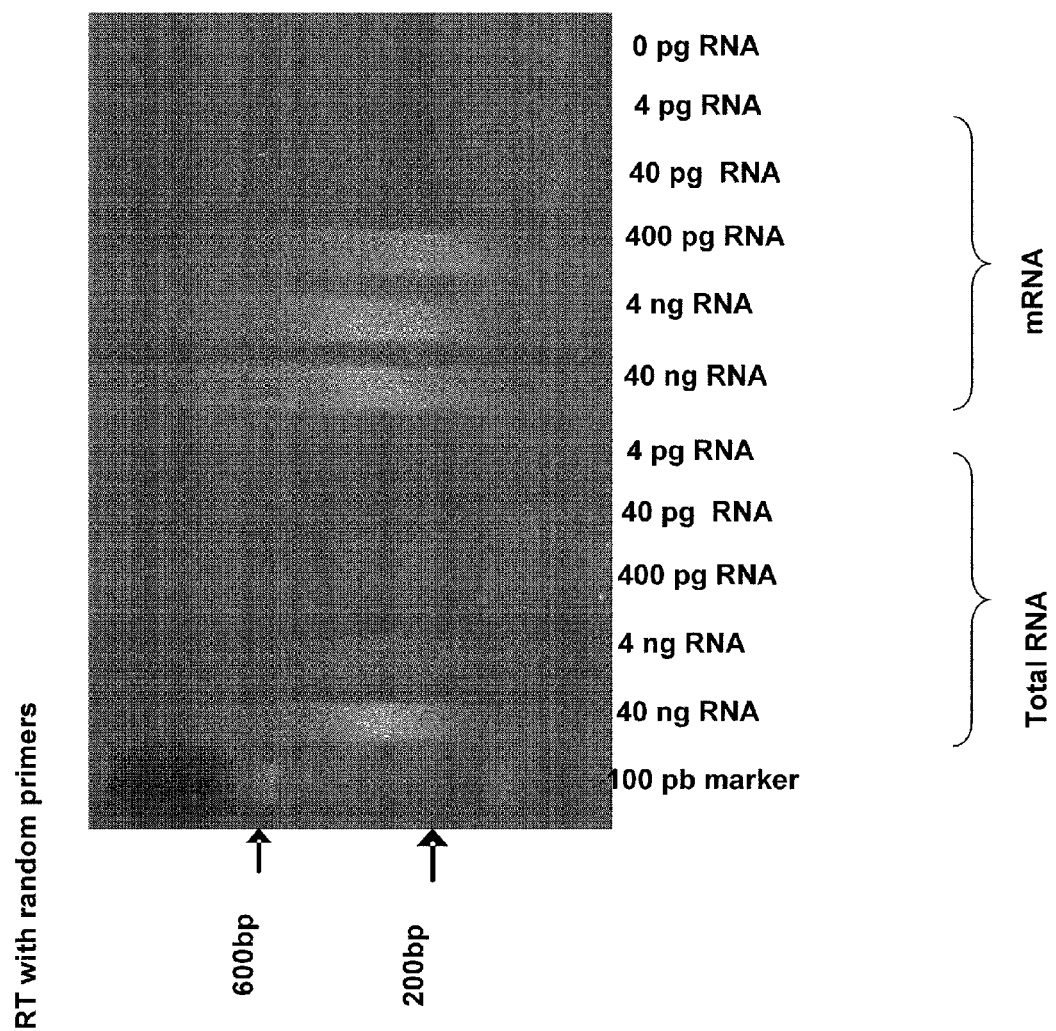
FIG. 10B depicts a gel showing the results of random primer RT priming and WTA efficiency of 8mer random primers as a function of target concentration for total RNA and mRNA.
Figure 10C:
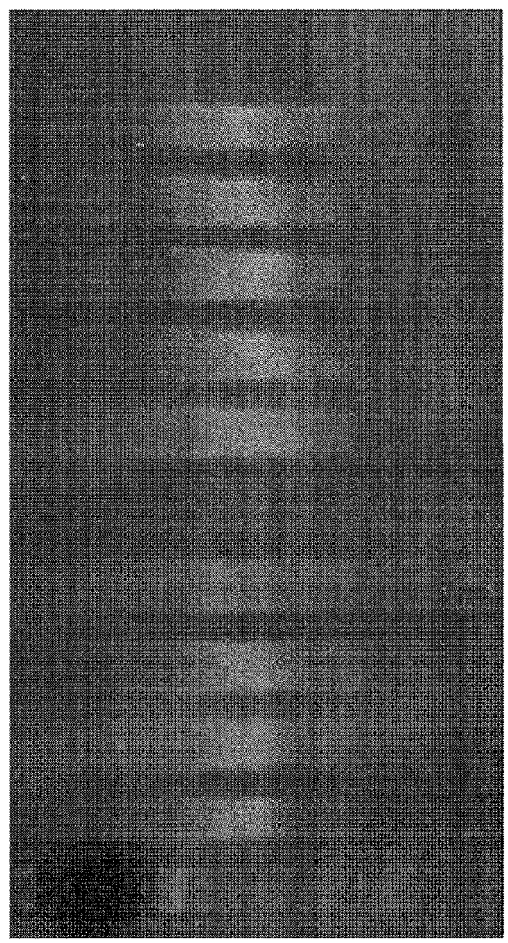
FIG. 10C depicts a gel showing the results of polyT target primer RT priming and WTA efficiency as a function of target concentration for total RNA and mRNA.

As shown in the results, a random primer RT approach can only effectively amplify inputs of total RNAs more than 4 ng (FIG. 10B, Table 1A). In contrast, the poly(T) target primer approach can amplify total RNAs down to 40 pg or roughly the amount of RNA in a single cell (FIG. 10C and Table 1B). Both Actb (Beta-Actin) and 18s rRNA were effectively amplified with random primer RT approach from mRNA (Table 1C) with Actb being amplified at subpicogram levels (data not shown).

In light of the results, it is clear that the use of the target primer allows for amplification of mRNA from total RNA. That is, the use of the target primer in the reverse transcription process allows one to amplify mRNA, without having to first isolate the mRNA from the total RNA.

Reproducibility

Figure 11:
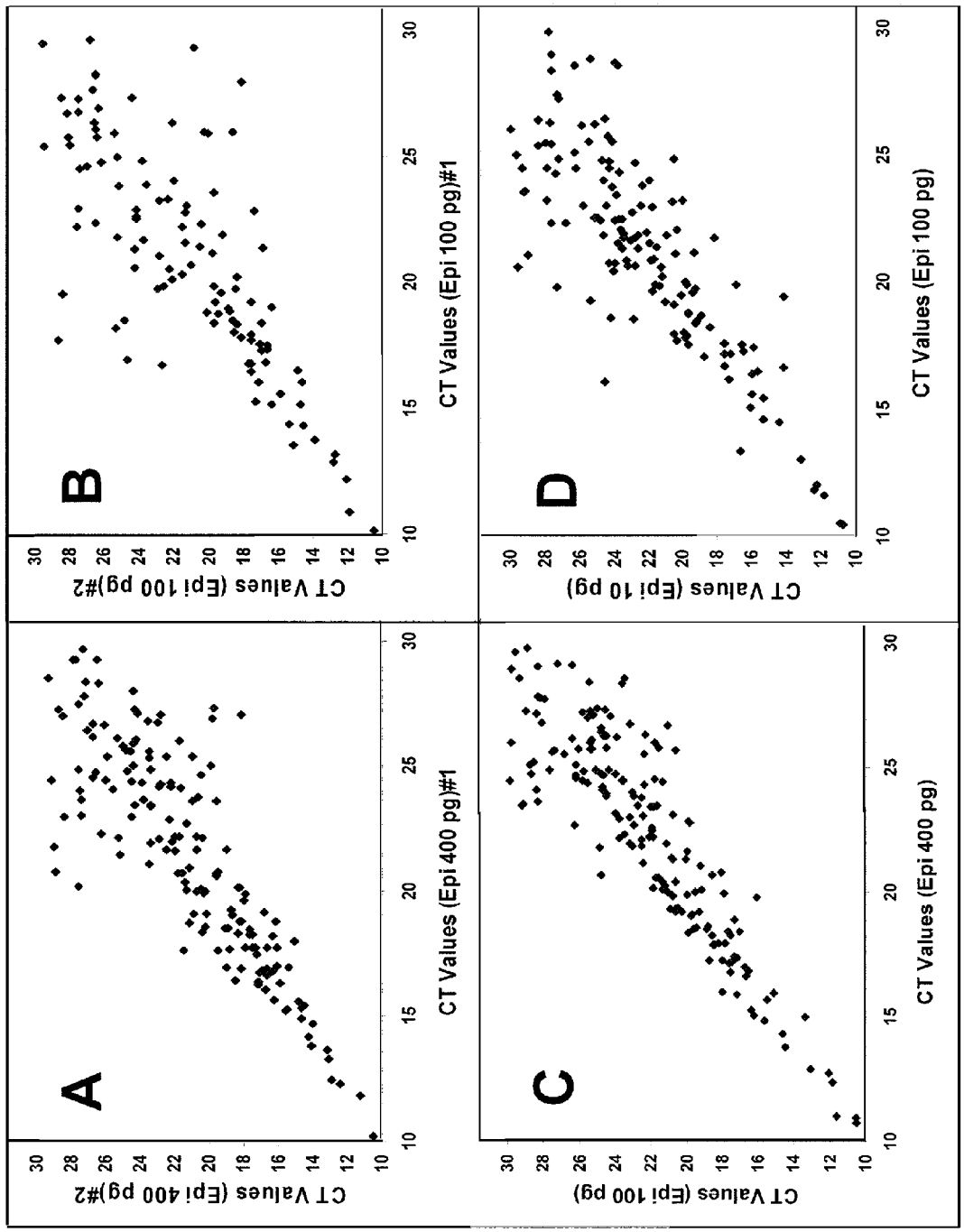
FIGS. 11A-11D depict the real time PCR scatter plots for 384 genes in whole transcriptome amplified cDNA.

To determine the reproducibility of the various protocols, parallel TaqMan reactions were performed for 384 genes on WTA reactions for 400 pg, 100 pg and 10 pg total RNAs. FIGS. 11A and 11B are the scatter plots of two representative WTA samples for 400 pg and 100 pg of mouse epiblast total RNAs, respectively. For genes with Ct values less than 25, the standard deviations, (SD), were mostly less than 2 Cts. The variations are significant for genes with Ct values larger than 25. The typical single copy cDNA detection of real-time PCR has Ct values 35-37. Because of the dilution factors inherent in the experimental design (see above) a Ct value of 25 corresponds to an abundance of 1-4 copies in the original samples. Therefore, large variations are to be expected for these genes simply because of stochastic considerations.

A useful test of the method is whether or not the relative abundance of expression of different genes is retained over a wide range of total RNA input. For genes with Ct values less than 25 (relatively abundant genes), the scatter correlation plot between 400 pg and 100 pg has Pearson coefficient=0.85 (FIG. 11C), the scatter correlation plot between 100 pg and 10 pg has Pearson coefficient=0.74 (FIG. 11D), and the scatter correlation plot between 10 pg and 1 pg has Pearson coefficient=0.68 (data not show). Therefore it appears that the relative abundance of multiple RNA species is maintained within acceptable levels down to RNA levels representing a small fraction of a cell.

Conclusion

In light of the above results, it is clear that single primer amplification following polyT target primer RT is a simple and efficient way of amplifying mRNA from single cell samples.

EXAMPLE 5

Impact of the Length of the 3' Target Specific Region

The influence of the length of the random primer serving as the 3' target specific region for the RT primer extension step was examined in this Example. The length of the random primer that serves as the 3' target specific region has two opposing factors. Longer regions are expected to prime more efficiently but have the potential of introducing increased numbers of base mismatches with increasing length. Therefore the shortest lengths that provide a useful amount of amplified DNA are best for massive parallel sequencing where relatively short lengths of sequence are read. Longer lengths of random priming are less critical for specifically targeted genes of known sequences because the vast majority of these sequences will be distal to the random priming sequences.

To determine the relative efficiency of RT random priming in relation to random primer length, 3' target specific regions having lengths of 5 to 12 nucleotides were used to amplify 4 ng of mouse total RNA (within the rest of the target primer arrangement described in Example 4).

Figure 12:
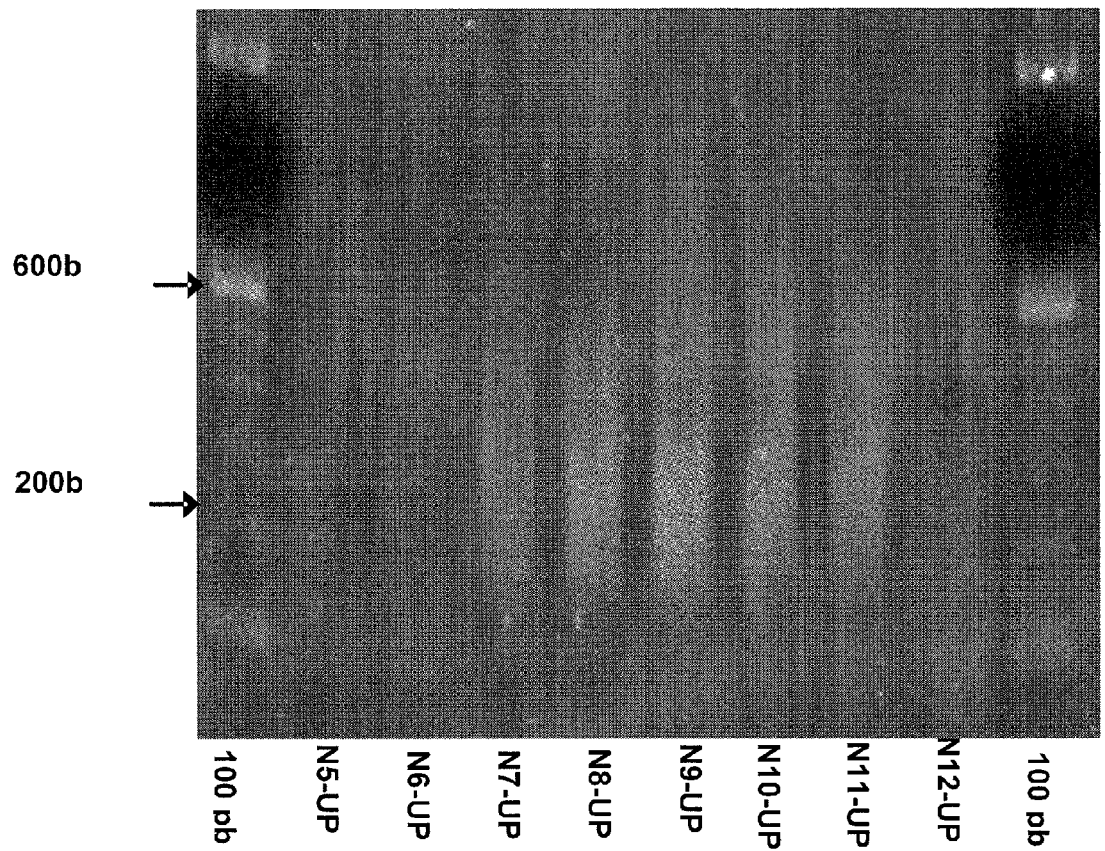
FIG. 12 depicts a gel comparing the results of random RT priming for random sequences of different lengths.

The results are depicted in FIG. 12. All random primer lengths examined amplified the target, with random sequences longer than 7 nucleotides priming with good efficiency. The size of the amplified sequences centers are 200-600 nucleotide pairs. The results presented in Example 4 employed a 3' target specific region of 8 random nucleotides.

In some embodiments, the above methods are combined with next generation sequencing in order to allow one to find many or all expressed transcripts in individual stem cells and other progenitor cells.

As will be appreciated by one of skill in the art, numerous insert amplification primers can be used for the above processing, e.g., 2-10, 10-50, 50-100, 100-1000, 1000-10,000, 10,000-30,000, 30,000-40,000, 40,000-50,000, 50,000-100,000, or more primers. Each can be used in a separate well with a representative portion of the amplified target nucleic acid sequence. As will be appreciated by one of skill in the art, in some embodiments, during the amplification, the conditions should be such that the shorter double-extended target primers rapidly self-hybridized, resulting in the selective amplification of the initially amplified products of the desired size.

While the above embodiments have often been described in terms of a linear primer, in other embodiments, the initial primer can be looped or need not be linear (as long as there is a universal region that is placed on one end and its complement is placed on the other end of a section of nucleic acid to be amplified. Thus, in some embodiments, any or every one of the above embodiments can be used with a stem-looped primer (or "loopable" primer) instead of a linear primer.

In this disclosure, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. The phrase "and/or" denotes a shorthand way of indicating that the specific combination is contemplated in combination and, separately, in the alternative.

The section headings used herein are for organizational purposes only and are not to be construed as limiting the described subject matter in any way.

It will be appreciated that there is an implied "about" prior to the temperatures, concentrations, times, etc. discussed in the present teachings, such that slight and insubstantial deviations are within the scope of the present teachings herein. For example, "a primer" means that more than one primer can, but need not, be present; for example but without limitation, one or more copies of a particular primer species, as well as one or more versions of a particular primer type, for example but not limited to, a multiplicity of different target primers. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for nucleic acid amplification, said method comprising:

producing an extended primer by performing a reverse transcription reaction on a target nucleic acid sequence using a first primer comprising a first 3' target specific region and a 5' universal region, wherein the first 3' target specific region comprises at least 6 thymines;

hybridizing a second primer to the extended primer, wherein the second primer comprises a second 3' target specific region and the 5' universal region;

extending a nucleic acid sequence from the second primer using the extended primer as the template for the extension, thereby forming a double extended primer;

allowing the double extended primer to self-hybridize, wherein the self hybridization occurs via the universal region and a sequence that is complementary to the universal region, thereby forming a looped section between the universal region and the sequence that is complementary to the universal region;

adding a third primer that is complementary to an insert section within the double extended target primer; and performing a PCR amplification to amplify the insert section.

2. The method of claim 1, wherein the second 3' target specific region comprises a splice site sequence or a sequence that is complementary to the splice site sequence, wherein the splice site sequence comprises the sequence 5'(A/C)AGG3'.

3. The method of claim 1, wherein the 3' target specific region further comprises a degenerate region, a random region, or a region that is degenerate and random.

4. The method of claim 1, further comprising the step of amplifying the double extended primer via at least one amplification primer.

5. The method of claim 4, wherein the amplification primer comprises the universal region.

6. The method of claim 1, wherein the first primer is a linear primer.

7. The method of claim 1, wherein the first primer is a loopable primer comprising:
a first loop forming region;
a noncomplementary region; and
a second loop forming region, wherein said first and second loop forming regions comprise nucleic acid sequences that are configured to hybridize to one another and wherein the noncomplementary region is located between the first and second loop forming regions.

8. The method of claim 1, wherein the first 3' target specific region further comprises a random sequence.

9. The method of claim 8, wherein the random sequence comprises at least two degenerate nucleotides.

10. The method of claim 1, wherein at least 10 different first primers are employed, wherein each of the 10 different first primers comprises a different first 3' target specific region.

11. The method of claim 1, wherein the looped section is less than 20 nucleotides in length.

12. The method of claim 1, further comprising the step of selectively amplifying at least a part of the double-extended primer that comprises a target nucleic acid sequence over a part of a different double-extended loopable primer that lacks a target nucleic acid sequence, apart from a 3' target specific region.

13. The method of claim 1, wherein the PCR amplification within the insert section is primed via an insert amplification primer, wherein the insert amplification primer hybridizes to a known nucleic acid sequence, the presence of which is desired to be detected.

14. The method of claim 1, wherein at least 10 insert amplification primers, each comprising a different nucleic acid sequence, are used for the PCR amplification within the looped section.

15. The method of claim 1, further comprising the step of removing random primers by a digestion of unpaired primers.

16. The method of claim 1, further comprising the step of amplifying the double extended primer via at least two amplification primers, wherein the first 3' target specific region comprises $T_n3'$ (SEQ ID NO: 5), wherein n=10-30 nucleotides, and the 5' universal region, and wherein the second 3' target specific region comprises the sequence 3' GGA(A/C) NN and the 5' universal region.

17. The method of claim 1, further comprising the step of amplifying the double extended primer via the use of an amplification primer, wherein the amplification primer consists essentially of the universal region.

18. The method of claim 1, wherein each element occurs in the order in which it is recited.

19. The method of claim 1, further comprising an incubation at a temperature of at least 90 degrees Celsius.

20. The method of claim 19, wherein the temperature is at least 95° C.

21. The method of claim 20, wherein the incubation lasts for at least 10 minutes.

22. The method of claim 19, wherein the incubation occurs after the reverse transcription reaction.

23. The method of claim 22, wherein the incubation occurs before hybridizing a second primer to the extended primer.

24. The method of claim 1, wherein the first primer further comprises a V or VN nucleotide or nucleotides, wherein V=A, C, or G.

25. A method for nucleic acid amplification, said method comprising:
performing a reverse transcription reaction on a target nucleic acid sequence to produce a cDNA of the target nucleic acid sequence;
introducing a universal region into the cDNA of the target nucleic acid sequence or the complement of the cDNA of the target nucleic acid sequence;
introducing a complement to the universal region into the cDNA of the target nucleic acid sequence or the complement of the cDNA of the target nucleic acid sequence, thereby forming a double extended target primer;
allowing the double extended target primer to self-hybridize, wherein the self hybridization occurs via the universal region and the complement to the universal region, thereby forming a looped section between the universal region and the sequence that is complementary to the universal region;
adding an insert primer that is complementary to an insert section within the double extended target primer; and
performing a PCR amplification to amplify the insert section.

26. The method of claim 25, wherein the complement to the universal region and the universal region are both introduced into the cDNA of the target nucleic acid sequence or the complement of the cDNA of the target nucleic acid sequence by hybridizing and extending a first target primer to either 1) the target nucleic acid sequence or 2) the cDNA of the target nucleic acid sequence, to produce an extended target primer and then hybridizing and extending a second target primer to the extended target primer to produce the double extended target primer.

27. The method of claim 25, wherein the reverse transcription reaction is primed using a first target primer that comprises a first 3' target specific region and the universal region, thereby forming an extended target primer.

28. The method of claim 27, wherein the first 3' target specific region comprises at least 6 thymines.

29. The method of claim 27, wherein the complement to the universal region is introduced by hybridizing a second target primer to the extended target primer and extending the second target primer along the extended target primer.

30. The method of claim 29, wherein the universal region is introduced through the second target primer, wherein the second target primer comprises a second 3' target specific region and the 5' universal region.

31. The method of claim 30, wherein the 3' target specific region of the first target primer comprises a random region.

32. The method of claim 30, wherein the 3' target specific region of the second target primer comprises a random region.

33. The method of claim 30, wherein the 3' target specific region of the second target primer comprises a splice site junction sequence.

34. The method of claim 30, wherein the 3' target specific region of the first target primer comprises a polyT region.

35. The method of claim 34, wherein the polyT region comprises at least 6 thymines.

* * * * *

SEQUENCE LISTING

<160> NUMBER OF SEQ ID NOS: 9

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt v                                                          11

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(42)
<223> OTHER INFORMATION: a, c, t, g, unknown or other
<220> FEATURE:
<221> NAME/KEY: misc_feature
<222> LOCATION: (31)..(42)
<223> OTHER INFORMATION: This region may encompass 5 to 12 nucleotides

<400> SEQUENCE: 2
tcatgatccg tggagtcggc tttttttttt nnnnnnnnnn nn                         42

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcatgatccg tggagtcggc tttttttttt                                      30

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tttttttttt tttttttttt v                                               21

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: This region may encompass 10 to 30 nucleotides

<400> SEQUENCE: 5
tttttttttt tttttttttt tttttttttt                                      30

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaaaaaaaa aaaaaaaa                                                    18

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 7
tttttttttt nn                                                          12

<210> SEQ ID NO 8
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (6)..(105)
<223> OTHER INFORMATION: This region may encompass 0 to 100 nucleotides

<400> SEQUENCE: 8
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaa         116

<210> SEQ ID NO 9
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (7)..(106)
<223> OTHER INFORMATION: This region may encompass 0 to 100 nucleotides

<400> SEQUENCE: 9
tttttttttt tttttttttt tttttttttt tttttttttt tttttttttt tttttttttt      60
tttttttttt tttttttttt tttttttttt tttttttttt tttttttttt tv             112
```